United States Patent
Ina et al.

(10) Patent No.: US 6,235,739 B1
(45) Date of Patent: May 22, 2001

(54) 5-PHENYL-3-PYRIDAZINONE DERIVATIVES AND DRUG COMPOSITION CONTAINING THE SAME

(75) Inventors: Shinji Ina; Kenjirou Yamana; Kyoji Noda, all of Omiya (JP)

(73) Assignee: Nikken Chemicals Co., Ltd., Tokyo (JP)

( * ) Notice: Subject to any disclaimer, the term of this patent is extended or adjusted under 35 U.S.C. 154(b) by 0 days.

(21) Appl. No.: 09/202,317

(22) PCT Filed: Jun. 6, 1997

(86) PCT No.: PCT/JP97/01925

§ 371 Date: Dec. 11, 1998

§ 102(e) Date: Dec. 11, 1998

(87) PCT Pub. No.: WO97/47604

PCT Pub. Date: Dec. 18, 1997

(30) Foreign Application Priority Data

Jun. 11, 1996 (JP) .................................................. 8-170723
Jun. 3, 1997 (JP) .................................................. 9-159273

(51) Int. Cl.[7] ......................... A61K 31/50; A61K 31/501; C07D 237/04
(52) U.S. Cl. ............... 514/247; 514/252.03; 514/252.01; 514/252.09; 514/252.05; 544/238; 544/239
(58) Field of Search ................................... 544/238, 239; 514/247, 252, 252.03, 252.04, 252.05, 252.01

(56) References Cited

U.S. PATENT DOCUMENTS 5,461,053 * 10/1995 Boigegrain et al. ................. 514/247

FOREIGN PATENT DOCUMENTS

| 2174472 | 10/1996 | (CA) . |
| 0 469 992 | 2/1992 | (EP) . |
| 0 738 715 | 10/1996 | (EP) . |
| 50-37800 | 4/1975 | (JP) . |
| 50-157360 | 12/1975 | (JP) . |
| 60-89421 | 5/1985 | (JP) . |
| 4-234369 | 8/1992 | (JP) . |
| 5-117239 | 5/1993 | (JP) . |
| 6-500071 | 1/1994 | (JP) . |
| 7-101861 | 4/1995 | (JP) . |
| WO91/15451 | 10/1991 | (WO) . |
| WO92/06963 | 4/1992 | (WO) . |
| WO94/10118 | 5/1994 | (WO) . |
| WO94/12461 | 6/1994 | (WO) . |
| WO95/03794 | 2/1995 | (WO) . |
| WO95/08534 | 3/1995 | (WO) . |

OTHER PUBLICATIONS

Nicholson et al, *TIPS*, vol. 121, pp. 19–27, 1991.*
Trends Pharm. Sci., 12, 19, (1991), Nicholson et al.
Thorax, 46, 512, (1991), Torphy et al.
J. Pharmacol. Exp. Ther., 266, 306 (1993), Underwood et al.
Br. J. Pharmacol., 112, 332 (1994), Teixeira et al.
Nature Medicine, 1, 244 (1994), Sommer et al.
Clin. Exp. Immunol., 100, 126 (1995), Sekut et al.

* cited by examiner

*Primary Examiner*—Emily Bernhardt
(74) *Attorney, Agent, or Firm*—Christie, Parker & Hale, LLP

(57) ABSTRACT

A 5-phenyl-3-pyridazinone derivative having the formula (I)

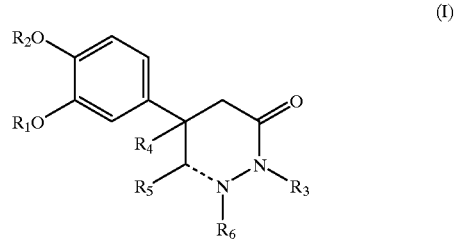

(I)

wherein $R_1$ represents an unsubstituted or substituted $C_1$ to $C_8$ alkyl group, $C_3$ to $C_7$ cycloalkyl group, or indanyl group; $R_2$ represents a $C_1$ to $C_4$ alkyl group; $R_3$ represents a hydrogen atom or an unsubstituted or substituted $C_1$ to $C_5$ alkyl group; a $C_3$ to $C_7$ cycloalkyl group; or an aryl group which may contain a heteroatom; $R_4$ and $R_5$ independently represent a hydrogen atom, $C_1$ to $C_6$ alkyl group, an unsubstituted or substituted phenyl, or a monocyclic aryl group which may contain a heteroatom; a dotted line represents a single or double bond, provided that when the dotted line represents a single bond; $R_6$ represents a hydrogen atom or $C_1$ to $C_6$ alkyl group.

7 Claims, No Drawings

5-PHENYL-3-PYRIDAZINONE DERIVATIVES AND DRUG COMPOSITION CONTAINING THE SAME

TECHNICAL FIELD

The present invention relates to a novel 5-phenyl-3-pyridazinone derivative having a type IV phosphodiesterase (PDE) inhibitory activity and a pharmaceutical composition containing the same.

BACKGROUND ART

Intracellular second messenger cAMP is synthesized by adenylate cyclase, and hydrolysed to 5'-AMP by a family of phosphodiesterase(PDE) isozymes. Up to now, at least five isozymes of PDE have been identified, and their distributions have been studied in variety of tissues [Trends Pharm. Sci., 12, 19, (1991)]. Among five PDE subtypes, type IV PDE was found to be a dominant isozyme in inflammatory cells. Increase in intracellular concentration of CAMP by inhibition of cAMP degradation with PDE inhibitors has been shown to inhibit several kind of inflammatory cells. In addition, airway smooth muscle tone are regulated by cAMP, increase in intracellular concentration of cAMP result in relaxation of airway smooth muscles [Thorax, 46, 512, (1991)]. Thus, a compound which inhibit type IV PDE may exhibit beneficial effects on inflammatory disease such as asthma [J. Pharmacol. Exp. Ther., 266, 306 (1993)], dermatitis [Br. J. Pharmacol., 112, 332 (1994)], and autoimmune diseases including multiple sclerosis [Nature Medicine, 1, 244 (1994)], and rheumatoid arthritis [Clin. Exp. Immunol., 100, 126 (1995)]. Because distribution of PDE isozymes are not same in different organs, specific inhibitor of type IV PDE may also decrease some adverse effects observed in nonspecific PDE inhibitor such as theophylline. Rolipram having the following formula (JP-A-50-157360 publication) is known as a compound having a specific inhibitory action against type IV PDE.

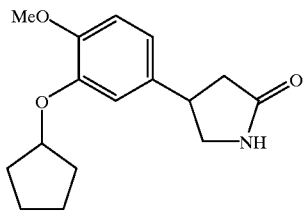

Other compounds having a specific inhibitory action against type IV PDE are known (WO 94/10118, WO 94/12461, JP-A-5-117259, JP-A-7-101861, WO 95/03794, WO 95/08534, etc.). However they have not been clinically applied up to now, and therefore, development of more useful compounds is desired.

JP-A-60-89421 discloses a compound having the following formula (II):

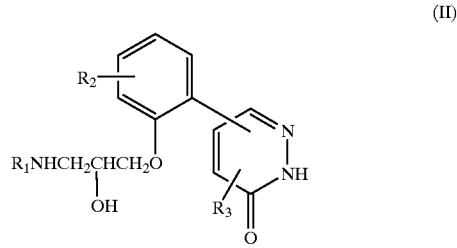

(II)

wherein $R_1$ represents an isopropyl group or t-butyl group; $R_2$ represents a hydrogen atom, $C_1$ to $C_4$ alkyl group, $C_1$ to $C_4$ alkoxy group, hydroxy group, or amino group; and $R_3$ represents a hydrogen atom or methyl group, as a β-adrenergic receptor antagonist. JP-A-4-234369 discloses a compound having the following formula (III):

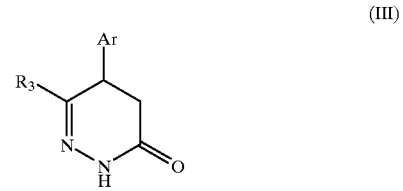

(III)

wherein Ar represents a phenyl group substituted with two groups, a pyridyl group, or thienyl group; and $R_3$ represents a $C_1$ to $C_5$ alkyl group, —$CH_2$Ph group, or —$CH_2CH_2$Ph group, as a synthesis intermediate of a pharmaceutical composition. JP-A-50-37800 discloses a compound having the following formula (IV):

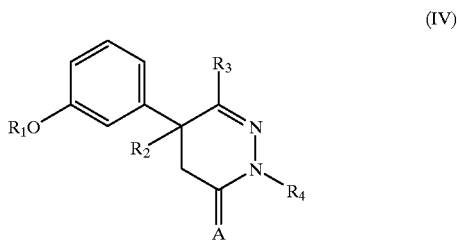

(IV)

wherein $R_1$, $R_2$, $R_3$, and $R_4$ represent a hydrogen atom or lower alkyl group; and A represents a hydrogen atom or oxygen atom, as a synthesis intermediate of a compound exhibiting an analgesic action. WO 92/06963 discloses a compound having the following formula (V):

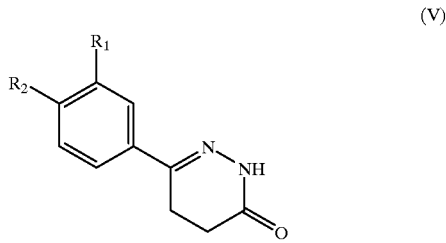

(V)

wherein $R_1$ and $R_2$ represent a methoxy group, difluoromethoxy group, ethoxy group, $C_4$ to $C_7$ cycloalkoxy group, or $C_3$ to $C_7$ cycloalkylmethoxy group, as a synthesis intermediate of a compound exhibiting a bronchospasm relieving action. However, the fact that the compound having the above formula (V) per se exhibits the bronchospasm relieving action is not described at all.

DISCLOSURE OF INVENTION

Accordingly, an object of the present invention is to provide a novel compound having a type IV PDE inhibitory activity, especially strong bronchodilator and anti-inflammatory effects, and a pharmaceutical composition containing the same.

In accordance with the present invention, there is provided a 5-phenyl-3-pyridazinone derivative having the following general formula (I):

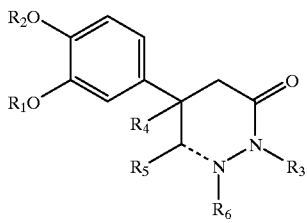

wherein $R_1$ represents an unsubstituted or substituted $C_1$ to $C_8$ alkyl, $C_3$ to $C_7$ cycloalkyl or indanyl group; $R_2$ represents a $C_1$ to $C_4$ alkyl group; $R_3$ represents a hydrogen atom; an unsubstituted or substituted $C_1$ to $C_5$ alkyl group; a $C_3$ to $C_7$ cycloalkyl group; or an aryl group which may contain at least one heteroatom selected from the group consisting of oxygen atom, nitrogen atom, and sulfur atom; $R_4$ and $R_5$ independently represent a hydrogen atom, a $C_1$ to $C_6$ alkyl group, an unsubstituted or substituted phenyl or a monocyclic aryl group which may contain at least one heteroatom selected from the group consisting of an oxygen atom, nitrogen atom, and sulfur atom; a dotted line represents a single or double bond, provided that when the dotted line represents a single bond, $R_6$ represents a hydrogen atom or $C_1$ to $C_6$ alkyl group), an optical isomer thereof, a pharmaceutically acceptable salt thereof, or a hydrate or solvate thereof.

BEST MODE FOR CARRYING OUT THE INVENTION

The present invention is described in detail below.

As $R_1$ of the above formula (I), a $C_1$ to $C_8$ linear or branched alkyl group (for example, a methyl, ethyl, propyl, isopropyl, n-butyl, isobutyl, sec-butyl, t-butyl, n-pentyl, 1,1-dimethylpropyl, 2,2-dimethylpropyl, 2-ethylbutyl, n-hexyl, 1-methylpentyl, 1,1-dimethylbutyl, n-heptyl, and n-octyl) may be mentioned. These may contain a substituent (for example, a phenyl; a cycloalkyl group such as a cyclopropyl, cyclobutyl, cyclopentyl and cyclohexyl and a cycloalkyl substituted with an alkyl group such as a methyl, ethyl, and propyl. As a specific substituted $C_1$ to $C_8$ alkyl group, for example, a cyclopropylmethyl, cyclobutylmethyl, cyclopentylmethyl, cyclohexylmethyl, benzyl, phenethyl, 3-phenylpropyl, 4-phenylbutyl, (1-methylcyclopropyl) methyl, and (1-phenylcyclopropyl)methyl may be mentioned. As $R_1$, a $C_3$ to $C_7$ cycloalkyl group (for example, a cyclopropyl, cyclobutyl, cyclopentyl, cyclohexyl, cycloheptyl, etc.) and indanyl may be mentioned. As $R_1$, preferably a $C_1$ to $C_6$ alkyl group, a $C_1$ to $C_5$ alkyl group which is substituted with a phenyl, $C_3$ to $C_7$ cycloalkyl group, or $C_3$ to $C_7$ cycloalkyl group substituted with a $C_1$ to $C_3$ alkyl group; $C_4$ to $C_6$ cycloalkyl group; or an indanyl group may be mentioned. More preferably a cyclopentyl, cyclopropylmethyl, or 2-indanyl may be mentioned.

As $R_2$, a $C_1$ to $C_4$ linear or branched alkyl group (for example, a methyl, ethyl, n-propyl, isopropyl, n-butyl, sec-butyl, and t-butyl) may be mentioned. Preferably a methyl or ethyl, more preferably a methyl, may be mentioned.

As $R_3$, a hydrogen atom; a $C_1$ to $C_5$ linear or branched alkyl group (for example, a methyl, ethyl, n-propyl, isopropyl, n-butyl, sec-butyl, t-butyl and n-pentyl) may be mentioned. These may be substituted with an aryl group which may contain at least one heteroatom selected from an oxygen atom, nitrogen atom, and sulfur atom (for example, a phenyl, pyridyl, thiazolyl, furyl, thienyl, naphthyl, and quinolyl). As the specific $C_1$ to $C_5$ alkyl group which may be substituted, for example a benzyl, phenethyl, 3-phenylpropyl, 4-phenylbutyl, 5-phenylpentyl, pyridylmethyl, furylmethyl, thiazolylmethyl, 1-naphthylmethyl, and 4-quinolylmethyl may be mentioned. Further, as $R_3$, a $C_3$ to $C_7$ cycloalkyl group (for example, a cyclopropyl, cyclobutyl, cyclopentyl, cyclohexyl, and cycloheptyl) and an aryl group which may contain at least one heteroatom selected from an oxygen atom, nitrogen atom, and sulfur atom (for example, a phenyl, pyridyl, thiazolyl, furyl, thienyl, naphthyl, and quinolyl) may be mentioned. As $R_3$, preferably a hydrogen atom, a $C_1$ to $C_3$ alkyl group, an aryl group, and a $C_1$ to $C_2$ alkyl group substituted with an aryl group may be mentioned. More preferably, a hydrogen atom, methyl, ethyl, phenyl, or benzyl may be mentioned.

As $R_4$ and $R_5$, a hydrogen atom; $C_1$ to $C_6$ linear or branched alkyl group (for example, a methyl, ethyl, propyl, isopropyl, butyl, sec-butyl, t-butyl, pentyl, and hexyl); a phenyl which may be substituted (for example, a phenyl, 4-methylphenyl, and 4-chlorophenyl); a monocyclic aryl group having at least one heteroatom selected from an oxygen atom, nitrogen atom, and sulfur atom (for example, a pyridyl group, thiazolyl group, thienyl group, and furyl group) may be independently mentioned. Preferably, as $R_4$ and $R_5$, a hydrogen atom, methyl, ethyl, phenyl, and pyridyl may be independently mentioned. More preferably, $R_5$ is a hydrogen atom.

A dotted line represents a single or double bond, provided that when the dotted line is a single bond, $R_6$ represents a hydrogen atom or $C_1$ to $C_6$ alkyl group (for example, a methyl group, ethyl group, propyl group, butyl group, pentyl group, and hexyl group). The dotted line preferably represents a double bond.

The compound represented by the above formula (I) has an asymmetric carbon atom and includes optical isomers. The optical isomers are also included in the present invention. Further, salts of the compound of the formula (I) and optical isomers thereof are included in the present invention. The salt is preferably a pharmaceutically acceptable salt. For example, salts of inorganic acids such as a salt of hydrochloric acid, hydrobromic acid, hydroiodic acid, and phosphoric acid and salts of organic acids such as a salt of oxalic acid, maleic acid, fumaric acid, lactic acid, malic acid, citric acid, tartaric acid, benzoic acid, methanesulfonic acid, and p-toluenesulfonic acid may be mentioned.

Further, the present invention includes a hydrate and a solvate of the compound having the formula (I), optical isomers thereof, and salts thereof. The solvents for the solvates include methanol, ethanol, isopropanol, butanol, acetone, ethyl acetate, chloroform, etc.

The compound having the above formula (I) can be produced by a known method (for example, see JP-A-50-37800, JP-A-60-89421, JP-A-4-234369, etc.) An example of the production process is described with reference to the following reaction schemes.

or ammonium acetate in an aromatic hydrocarbon solvent such as benzene and toluene which does not inhibit the reaction. The reaction product is separated by a known method and is used for the next step without further purification.

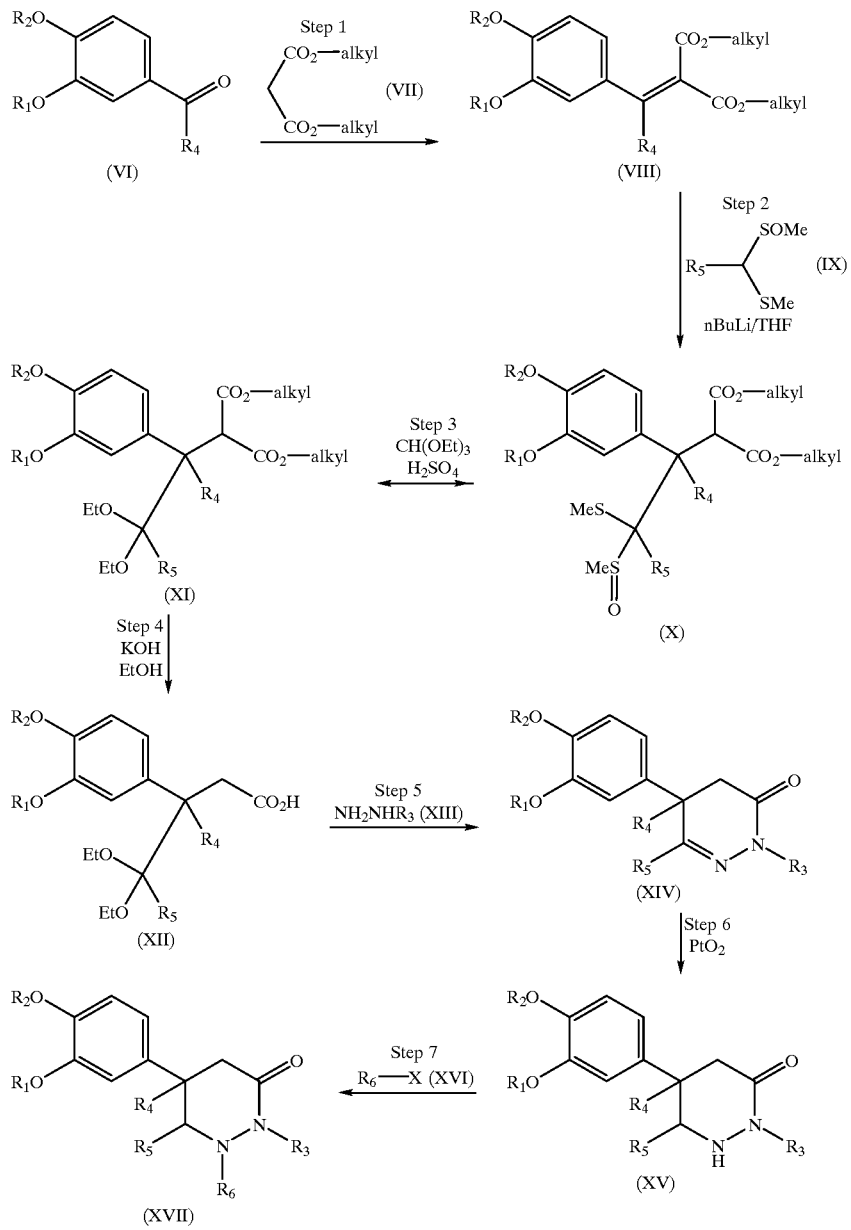

Process of Production 1

The compounds (XIV), (XV), and (XVII) each corresponds to the compound having the formula (I).

Step 1

α,β-unsaturated dialkyl ester (VIII) is synthesized from a ketone derivative (or an aldehyde derivative when $R_4$ represents a hydrogen atom) (VI) and a dialkyl ester derivative of malonic acid (VII) by a Knoevenagel reaction. Generally, the reaction is performed in the presence of a base such as an amine such as piperidine, an organic acid salt of an amine, Step 2

Methyl methylsulfinyl-methylsulfide (IX) is reacted with α,β-unsaturated dialkyl ester (VIII) in the presence of a base such as n-butyllithium to synthesize thioether (X) [J. L. Hermann et al., Tetrahedron Letters 47, 4707, (1973)]. Generally, an ether solvent such as diethyl ether or tetrahydrofuran is used as a reaction solvent, and the reaction is performed at a temperature of 0° C. or less. The methyl methylsulfinyl-methylsulfide (IX) used here is prepared by a known method [Ogura et al., Tetrahedron Letters, 659, (1974)].

Step 3

Thioether (X) is reacted with triethyl orthoformate in the presence of a catalytic amount of an acid such as sulfuric acid to synthesize diethyl acetal (XI). The reaction product is separated by a known method.

Step 4

Diethyl acetal (XI) is hydrolyzed with a base, is then decarboxylated, and is further treated with an acid to be converted to 3-phenyl butyric acid (XII). The base usable in the hydrolysis is, for example, potassium hydroxide and sodium hydroxide, and the solvent usable includes water or an alcohol (ethanol, methanol, etc.)

Step 5

3-phenylbutyric acid (XII) is reacted with a hydrazine (XIII) to synthesize 2,3,4,5-tetrahydro-pyridazin-3-one (XIV). The reaction is performed in the presence or absence of a solvent. Any solvent may be used so long as it does not inhibit the reaction. For example, benzene, toluene, xylene, methanol, ethanol, isopropanol, butanol, decaline, tetraline, acetic acid, water, etc. may be mentioned. The reaction temperature is generally about 0 to 120° C. The reaction product is purified by a known method such as crystallization, recrystallization, and chromatography.

Step 6

2,3,4,5-tetrahydropyridazin-3-one (XIV) is converted to hexahydropiridazin-3(2H)-one (XV) by a reducing agent. The reducing agent usable here is preferably platinum oxide. The reaction product is purified by a known method.

Step 7

An alkyl halide (XVI) is reacted with hexahydropyridazin-3-one (XV) in the presence of a base to synthesize a compound (XVII). X in the formula of the compound (XVI) represents a halogen atom (e.g., chlorine atom, bromine atom, iodine atom, etc.). The base used for the reaction includes, for example, sodium hydroxide, potassium hydroxide, sodium hydride, triethylamine, pyridine, etc. The reaction is performed in the presence or absence of a solvent. Any solvent may be used so long as it does not inhibit the reaction. For example, benzene, toluene, xylene, tetrahydrofuran, diethyl ether, dimethylformamide, dimethyl sulfoxide, dichloromethane, chroloform, etc. may be mentioned. The reaction product is purified by a known method.

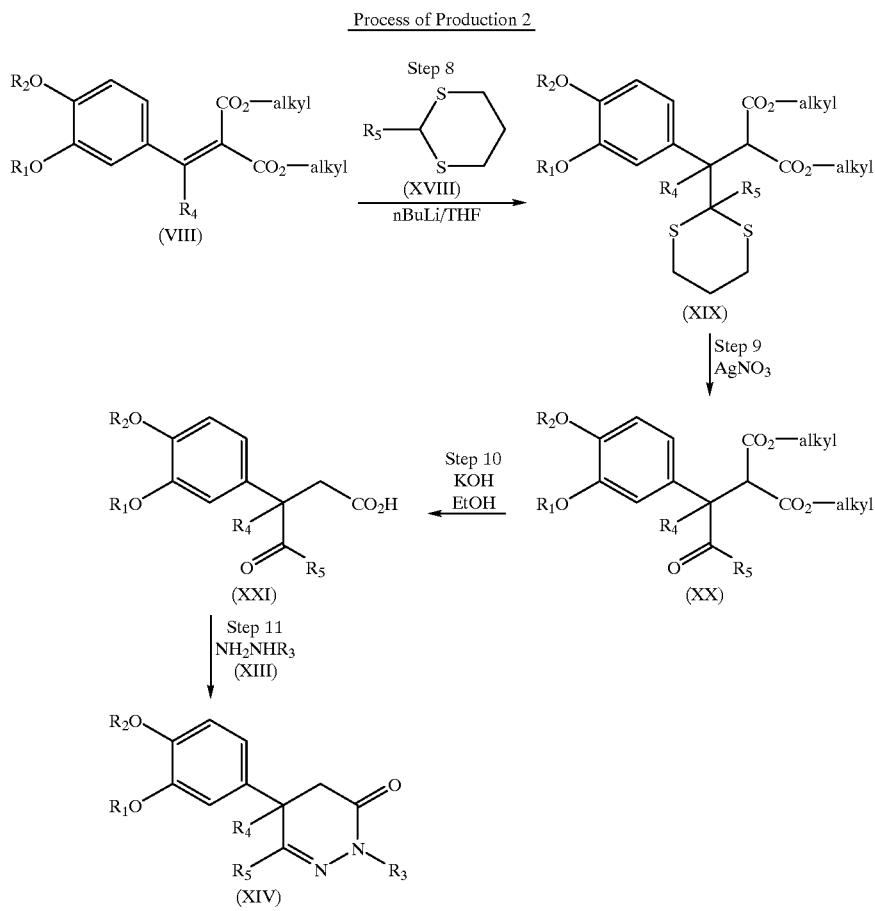

Process of Production 2

The compound (XIV) in the reaction scheme corresponds to a compound (I) having the formula (I).

Step 8

A 1,3-dithiane (XVIII) is reacted with α,β-unsaturated dialkyl ester (VIII) in the presence of a base such as n-butyllithium to synthesize 1,3-dithiane (XIX).

Step 9

1,3-dithiane (XIX) is deprotected by a known method to synthesize 4-ketobutyric acid ester (XX).

Step 10

A 4-ketobutyric acid ester (XX) is converted to 4-ketobutyric acid (XXI) by the same method as in the Step 4.

Step 11

Using the same method as in Step 5, 4-ketobutyric acid (XXI) is reacted with a hydrazine (XIII) to synthesize 2,3,4,5-tetrahydro-pyridazin-3-one (XIV).

Process of Production 3

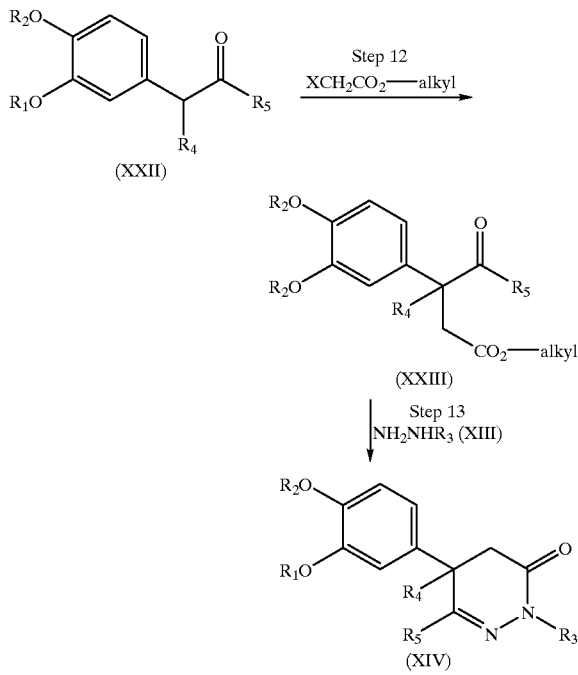

The compound (XIV) in the above reaction scheme corresponds to a compound having the formula (I).

Step 12

A ketone derivative (or an aldehyde derivative when $R_5$ is a hydrogen atom) (XXII) is reacted with a halogenated acetic acid ester in the presence of a base to synthesize a 4-ketobutyric acid ester (XXIII).

Step 13

A 4-ketobutyric acid ester (XXIII) is reacted with a hydrazine (XIII) by the same method as in Step 5 to synthesize 2,3,4,5-tetrahydropyridazin-3-one (XIV).

The starting material usable for the above reaction step is a commercially available compound or is synthesized by a known method from existing compounds. The starting ketone derivative (VI) can be prepared by a method disclosed in WO94/10118.

When the compound of the invention is used as a therapeutic agent, it can be administered alone or together with a pharmacologically acceptable carrier. The composition is determined by the solubility of the compound, its chemical properties, the delivery route, medication plan, etc. For instance, it can be administered orally in the form of granules, powders, tablets, pills, hard gelatin capsules, soft gelatin capsules, syrups, emulsions, suspensions, liquids, etc. or can be administered by a non-oral route such as an injection (e.g., intravenous, intramuscular, or hypodermic injection), ointment, suppository, aerosol, etc. Alternatively, it may be made a powder for injection which is prepared at the time of use. Organic or inorganic solid or liquid carriers or diluents which are suitable for oral, rectal, non-oral, and topical administration can be used together with the compound of the invention. For example, in the case of the oral administration, the compound can be prepared in the desired form by using excipients such as lactose, D-glucose, corn starch, and sucrose, disintegrants such as calcium carboxymethylcellulose, hydroxypropylcellulose, etc., lubricants such as calcium stearate, magnesium stearate, talc, polyethylene glycol, and hydrogenated oil, humectants such as hydroxypropylcellulose, hydroxypropylmethylcellulose, carboxymethylcellulose, polyvinyl alcohol, gelatin, and gum arabic, and a surfactant and flavoring agent if necessary.

When non-orally administered, it is possible to use a diluent such as water, ethanol, glycerol, propylene glycol, polyethylene glycol, agar, and tragacanth and, if necessary, use a solution adjuvant, buffering agent, preservative, flavoring agent, and colorant, etc. Pharmaceutical compositions may be prepared by general methods.

The clinical dosage generally ranges 0.01 to 1000 mg in terms of the compound of the invention per adult per day when orally administered, preferably 0.01 to 100 mg, but can be appropriately arranged depending upon the age, condition, symptoms, other drugs administered at the same time, etc. The daily dosage of the drug (i.e., compound of present invention) can be administered once a day or twice or three times a day with suitable intervals or intermittently. When administered by injection, one dosage in an amount of 0.001 to 100 mg per adult with or without intervals is preferable.

EXAMPLES

Below, the present invention will be explained in detail with references to the Examples and Test Examples, but is not limited thereto.

Example 1

Synthesis of 5-(3,4-dimethoxyphenyl)-2,3,4,5-tetrahydropyridazin-3-one (Compound No. 1 shown in Table (1)

(1) 3,4-dimethoxybenzylidenemalonic acid diethyl ester 9.13 g (55 mM) of 3,4-Dimethoxybenzaldehyde (veratraldehyde) was heated in 100 ml of benzene together with 8.00 mg (50 mM) of diethyl malonate, 0.29 ml of acetic acid, and 0.74 ml of piperidine in an apparatus equipped with a water separation tube (i.e., Dean Stark tube) until 50 mM water was separated. The benzene solution was washed with water and was dried over anhydrous magnesium sulfate. After being dried, the benzene was evaporated in vacuo to obtain 15.40 g crude product. The crude product obtained here had a sufficient purity even without purification, thus could be used as it was in the following step.

$^1$H-NMR (CDCl$_3$, 400 MHz) δ1.33 (3H,t, J=7.32 Hz), 1.33 (3H, t, J=7.32Hz), 3.87 (3H, s), 3.91 (3H, s), 4.29 (2H, q, J=7.32 Hz), 4.35 (2H, q, J=7.35 Hz), 6.86 (1H, d, J=8.30 Hz), 7.03 (1H, d, J=1.95 Hz), 7.09 (1H, dd, J=8.30, 1.95 Hz), 7.66 (1H, s)

(2) 3-(3,4-dimethoxyphenyl)-4,4-diethoxy-2-ethoxycarbonylbutyric acid ethyl ester 24 ml of dried tetrahydrofuran solution of 2.34 g (18.81 mM) of methyl methylsulfinyl-methyl sulfide was cooled to 0° C. A hexane solution of n-butyl lithium (18.81 mM) was added dropwise to the solution and was stirred for around 30 minutes at the same temperature. The solution was cooled to −78° C., and solution of 5.00 g (15.47 mM) 3,4-dimethoxybenzylidenemalonic acid diethyl ester in 2 ml of dried tetrahydrofuran was added. The solution thus obtained was heated gradually to room temperature, poured to an aqueous ammonium chloride solution, and was extracted with diethyl ether. The organic extract was dried over anhydrous magnesium sulfate, then the solvent was evaporated in vacuo to obtain 6.70 g crude product of brown oily 3-(3,4-dimethoxyphenyl)-2-ethoxycarbonyl-4-methylsulfinyl-4-methylthiobutyric ethyl ester. The crude product was dissolved in 25 ml of anhydrous ethanol, 3.09 g (20.88 mM) of ethyl orthoformate and 0.25 ml of sulfuric acid were added thereto, and the mixture was stirred for 3 days at room temperature. The solution was poured to an aqueous sodium hydrogencarbonate under ice cooling and was extracted with diethyl ether. The organic extract was dried, then the solvent was evaporated in vacuo to obtain a brown oily crude product. The crude product was purified by chromatography. The product was concentrated and dried in vacuo to obtain 5.08 g of yellow oily 3-(3,4-dimethoxyphenyl)-4,4-diethoxy-2-ethoxycarbonylbutyric acid ethyl ester (yield 79.5%).

(3) 5-(3,4-dimethoxyphenyl)-2,3,4,5-tetrahydropyridazin-3-one 3.07 g (7.44 mM) of 3-(3,4-dimethoxyphenyl)-4,4-diethoxy-2-ethoxycarbonylbutyric acid ethyl ester and 3.41 g of potassium hydroxide were heated at reflux for 4 hours in 40 ml of ethanol. The solution was poured to water, was acidified with concentrated hydrochloric acid, and was extracted with diethyl ether. The organic extract was dried over anhydrous magnesium sulfate and the solvent was evaporated in vacuo to obtain 1.98 g of brown oily 3-(3,4-dimethoxyphenyl)-4,4-diethoxybutyric acid. 1.98 g of the brown oily product thus obtained and 0.90 ml of hydrazine hydrate were added to a mixed solution of 8.3 ml of acetic acid and 6.3 ml of water. The solution was heated at reflux for 5 hours, poured to an aqueous sodium hydrogencarbonate solution, extracted with methylene chloride, and dried. The solvent was evaporated in vacuo to obtain a yellow solid residue. The residue was purified by flash chromatography ($SiO_2$: eluted with a gradient of 60% ethyl acetate/hexane to 70% ethyl acetate/hexane). The solvent was evaporated in vacuo and the resultant product was dried to obtain 0.92 g of a light yellow solid of the above-described compound (yield 53.0%).

$^1$H-NMR ($CDCl_3$, 400 MHz) δ2.63 (1H, dd, J=17.09, 11.23 Hz), 2.82 (1H, dd, J=17.09, 7.81 Hz), 3.81 (1H, ddd, J=11.23, 7.81, 2.44 Hz), 3.89 (3H, s), 3.89 (3H, s), 6.71 (1H, d, J=1.96 Hz), 6.77 (1H, dd, J=8.30, 1.96 Hz), 6.87 (1H, d, J=8.30 Hz), 7.18 (1H, d, J=2.44 Hz), 8.48 (1H, broad s)

Example 2

Synthesis of 5-(3,4-dimethoxyphenyl)-2-phenyl-2,3,4,5-tetrahydropyridazin-3-one (Compound No. 2 shown in Table 1)

3.28 g (12.32 mM) of 3-(3,4-dimethoxyphenyl)-4,4-diethoxybutyric acid obtained in Example 1(3) and 3.33 g (30.79 mM) of phenylhydrazine were added to a mixed solution of 16 ml of acetic acid and 11 ml of water. The solution was heated at reflux for 5 hours, was poured to an aqueous sodium hydrogencarbonate solution, and was extracted with methylene chloride. The organic extract was dried over anhydrous sodium sulfate and the solvent was evaporated in vacuo to obtain a brown oily product. The product was purified by flash chromatography ($SiO_2$: eluted with a gradient of 20% of ethyl acetate/hexane to 50% of ethyl acetate/hexane). The solvent was evaporated in vacuo and the resultant product was dried to obtain 0.35 g of a light yellow solid of the above-described compound (yield 9.1%).

$^1$H-NMR ($CDCl_3$, 400 MHz) δ2.83 (1H, dd, J=16.60, 11.23 Hz), 3.00 (1H, dd, J=16.60, 7.33 Hz), 3.89 (6H, s), 3.93 (1H, m), 6.76 (1H, d, J=1.95 Hz), 6.82 (1H, dd, J=8.30, 1.95 Hz), 6.89 (1H, d, J=8.30 Hz), 7.29 (1H, d, J=7.33 Hz), 7.40–7.44 (3H, m), 7.50–7.52 (2H, m)

Example 3

Synthesis of 5-(3-cyclopentyloxy-4-methoxyphenyl)-2,3,4,5-tetrahydropyridazin-3-one (Compound No. 3 shown in Table 1)

(1) 3-cyclopentyloxy-4-methoxybenzylidenemalonic acid diethyl ester

Using the same procedure as in Example 1(1), 3-cyclopentyloxy-4-methoxybenzaldehyde, instead of 3,4-dimethoxybenzaldehyde, was used to obtain 3-cyclopentyloxy-4-methoxybenzylidenemalonic acid diethyl ester.

$^1$H-NMR ($CDCl_3$, 400 MHz) δ1.33 (6H, t, J=6.83 Hz), 1.58–1.64 (2H, m), 1.79–2.00 (6H, m), 3.87 (3H, s), 4.29 (2H, q, J=6.83 Hz), 4.35 (2H, q, J=6.83 Hz), 4.72 (1H, m), 6.84 (1H, d, J=8.30 Hz), 7.04–7.07 (2H, m), 7.64 (1H, s)

(2) 3-(3-cyclopentyloxy-4-methoxyphenyl)-4,4-diethoxy-2-ethoxycarbonylbutyric acid ethyl ester Using the same procedure as in Example 1(2), 3-cyclopentyloxy-4-methoxybenzylidenemalonic diethyl ester, instead of 3,4-dimethoxybenzylidenemalonic acid diethyl ester, was used to obtain 3-(3-cyclopentyloxy-4-methoxyphenyl)-4,4-diethoxy-2-ethoxycarbonylbutyric acid ethyl ester (yield 89.4%).

(3) 5-(3-cyclopentyloxy-4-methoxyphenyl)-2,3,4,5-tetrahydropyridazin-3-one

Using the same procedure as in Example 1(3), 3-(3-cyclopentyloxy-4-methoxyphenyl)-4,4-diethoxy-2-ethoxycarbonylbutyric acid ethyl ester, instead of 3-(3,4-dimethoxyphenyl)-4,4-diethoxy-2-ethoxycarbonylbutyric acid ethyl ester, was used to obtain a light yellow solid of the above-described compound (yield 68.9%) via 3-(3-cyclopentyloxy-4-methoxyphenyl)-4,4-diethoxybutyric acid.

$^1$H-NMR ($CDCl_3$, 400 MHz) δ1.58–1.65 (2H, m), 1.81–1.96 (6H, m), 2.61 (1H, dd, J=17.09, 7.82 Hz), 2.81 (1H, dd, J=17.09, 11.72 Hz), 3.75–3.80 (1H, m), 3.84 (6H, s), 4.74–4.77 (1H, m), 6.71 (1H, d, J=1.94 Hz), 6.74 (1H, dd, J=8.30, 1.94 Hz), 6.85 (1H, d, J=8.30 Hz), 7.17 (1H, d, J=2.45 Hz), 8.54 (1H, broad s)

Example 4

Synthesis of 5-(3-cyclopentyloxy-4-methoxyphenyl) hexahydropyridazin-3-one (Compound No. 4 shown in Table 1)

0.40 g (1.39 mM) of 5-(3-cyclopentyloxy-4-methoxyphenyl)-2,3,4,5-tetrahydropyridazin-3-one obtained in Example 3 was dissolved in a solution of 8 ml of ethanol and 0.12 ml of acetic acid. 0.13 g of platinum oxide (IV) was added to the solution, and the solution was stirred under a stream of hydrogen at atmospheric pressure at room temperature. After 6 hours, the solution was filtered, the filtrate was concentrated in vacuo, an aqueous sodium hydrogencarbonate solution was added to the residue obtained, and the result was extracted with methylene chloride. The organic extract was dried over anhydrous sodium sulfate and the solvent was evaporated in vacuo to obtain a crude product. The crude product was purified by flash chromatography ($SiO_2$: eluted with a gradient of 2% methanol/methylene chloride to 5% methanol/methylene chloride). The solvent was removed under vacuum and the resultant product was dried to obtain 0.35 g of a white solid of the above-described compound (yield 85.9%).

$^1$H-NMR ($CDCl_3$, 400 MHz) δ1.57–1.65 (2H, m), 1.79–1.96 (6H, m), 2.67 (1H, dd, J=18.07, 7.32 Hz), 2.86 (1H, dd, J=18.07, 7.32 Hz), 2.97–3.02 (1H, m), 3.20–3.34 (2H, m), 3.84 (3H, s), 4.07 (1H, broad s), 4.76 (1H, m), 6.70–6.73 (2 H, m), 6.85 (1H, d, J=1.81 Hz), 7.11 (1H, broad s)

Example 5

Synthesis of 5-(3-cyclopentyloxy-4-methoxyphenyl)-2-methyl-2,3,4,5-tetrahydropyridazin-3-one (Compound No. 5 shown in Table 1)

1.48 g (4.62 mM) of 3-(3-cyclopentyloxy-4-methoxyphenyl)-4,4-diethoxybutyric acid obtained in Example 3(3) and 0.43 g (9.24 mM) of methylhydrazine were refluxed under heating in a solution of 4 ml of acetic acid and 2.5 ml of water for 5 hours. In the following operation the same procedure as in Example 1(3) was used to obtain 0.68 g of a yellow solid of above-described compound (yield 48.8%).

$^1$H-NMR ($CDCl_3$, 400 MHz) δ1.60–1.65 (2H, m), 1.81–1.95 (6H, m), 2.60 (1H, dd, J=16.60, 11.72 Hz), 2.79 (1H, dd, J=16.60, 7.81 Hz), 3.40 (3H, s), 3.75 (1H, m), 3.84 (3H, s), 4.75 (1H, m), 6.69–6.73 (2H, m), 6.85 (1H, d, J=7.82 Hz), 7.19 (1H, d, J=1.95 Hz)

Example 6

Synthesis of 2-benzyl-5-(3-cyclopentyloxy-4-methoxyphenyl)-2,3,4,5-tetrahydropyridazin-3-one (Compound No. 6 shown in Table 1)

0.73 g (2.28 mM) of 3-(3-cyclopentyloxy-4-methoxyphenyl)-4,4-diethoxybutyric acid obtained in Example 3(3) and 0.36 g (2.28 mM) benzylhydrazine hydrochloride were heated at reflux in a solution of 2 ml of acetic acid and 1.3 ml of water for 5 hours. In the following operation, the same procedure as in Example 1(3) was used to obtain 0.34 g of a brown solid of the above-described compound (yield 39.5%).

$^1$H-NMR ($CDCl_3$, 400 MHz) δ1.55–1.61 (2H, m), 1.64–1.92 (6H, m), 2.65 (1H, dd, J=16.60, 11.72 Hz), 2.83 (1H, dd, J=16.60, 7.33 Hz), 3.75 (1H, m), 3.83 (3H, s), 4.67 (1H, m), 4.96 (1H, d, J=14.65 Hz), 5.00 (1H, d, J=14.65 Hz), 6.65 (1H, d, J=1.95 Hz), 6.67 (1H, dd, J=8.30, 1.95 Hz), 6.81 (1H, d, J=8.30 Hz), 7.22 (1H, d, J=2.44 Hz), 7.27–7.38 (5H, m)

Example 7

Synthesis of 5-(3-benzyloxy-4-methoxyphenyl)-2,3,4,5-tetrahydropyridazin-3-one (Compound No. 7 shown in Table 1)

(1) 3-benzyloxy-4-methoxybenzylidenemalonic acid diethyl ester

Using the same procedure as in Example 1(1), 3-benzyloxy-4-methoxybenzaldehyde, instead of 3,4-dimethoxybenzaldehyde, was used to obtain 3-benzyloxy-4-methoxybenzylidenemalonic acid diethyl ester.

$^1$H-NMR ($CDCl_3$, 400 MHz) δ1.29 (3H, t, J=7.33 Hz), 1.32 (3H, t, J=6.83 Hz), 4.27 (2H, q, J=6.83 Hz), 4.28 (2H, q, J=7.33 Hz), 3.91 (3H, s), 5.12 (2H, s), 6.88 (1H, d, J=8.30 Hz), 7.07 (1H, d, J=1.95 Hz), 7.10 (1H, dd, J=8.30, 1.95 Hz), 7.31 (1H, m), 7.38 (2H, dd, J=7.82, 6.83 Hz), 7.43 (2H, d, J=7.81 Hz), 7.61 (1H, s)

(2) 3-(3-benzyloxy-4-methoxyphenyl)-4,4-diethoxy-2-ethoxycarbonylbutyric acid ethyl ester Using the same procedure as in Example 1(2), 3-benzyloxy-4-methoxybenzylidenemalonic acid diethyl ester, instead of 3,4-dimethoxybenzylidenemalonic acid diethyl ester, was used to obtain 3-(3-benzyloxy-4-methoxyphenyl)-4,4-diethoxy-2-ethoxycarbonylbutyric acid ethyl ester (yield 67.3%).

(3) 5-(3-benzyloxy-4-methoxyphenyl)-2,3,4,5-tetrahydropyridazin-3-one

Using the same procedure as in Example 1 (3), 3-(3-benzyloxy-4-methoxyphenyl)-4,4-diethoxy-2-ethoxycarbonylbutyric acid ethyl ester, instead of 3-(3,4-dimethoxyphenyl)-4,4-diethoxy-2-ethoxycarbonylbutyric acid ethyl ester, was used to obtain a light yellow solid of the above-described compound (yield 77.1%) via 3-(3-benzyloxy-4-methoxyphenyl)-4,4-diethoxybutyric acid.

$^1$H-NMR ($CDCl_3$, 400 MHz) δ2.53 (1H, dd, J=17.09, 11.23 Hz), 2.75 (1H, dd, J=17.09, 7.81 Hz), 3.73 (1H, m), 3.89 (3H, s), 5.15 (2H, s), 6.71 (1H, d, J=1.95 Hz), 6.77 (1H, dd, J=8.30, 1.95 Hz), 6.89 (1H, d, J=8.30 Hz), 7.10 (1H, d, J=2.44 Hz), 7.31 (1H, m), 7.37 (2H, dd, J=7.81, 7.81 Hz), 7.42 (2H, d, J=7.81 Hz), 8.37 (1H, broad s)

Example 8

Synthesis of 5-(4-methoxy-3-phenethyloxyphenyl)-2,3,4,5-tetrahydropyridazin-3-one (Compound No. 8 shown in Table 1)

(1) 4-methoxy-3-phenethyloxybenzaldehyde 2.00 g (13.14 mM) of isovanillin, 1.61 g (13.14 mM) of phenethyl alcohol, and 4.14 g (15.77 mM) of triphenylphosphine were dissolved in 50 ml of dried tetrahydrofuran. 2.75 g (15.77 mM) of diethyl azodicarboxylate was dropwise added carefully at room temperature. After stirring overnight at room temperature, the solution was diluted with 100 ml of diethyl ether and washed with an aqueous sodium hydroxide solution and water in this order. The organic solution was dried over anhydrous magnesium sulfate and the solvent was evaporated in vacuo to obtain a light yellow oily residue. The residue was purified by flash chromatography ($SiO_2$: eluted with 25% hexane/ethyl acetate). The solvent was evaporated in vacuo and the result was dried to obtain 2.88 g of light yellow oily 4-methoxy-3-phenetyloxybenzaldehyde (yield 85.5%).

$^1$H-NMR ($CDCl_3$, 400 MHz) δ3.19 (2H, t, J=7.33 Hz), 4.28 (2H, t, J=7.33 Hz), 6.98 (1H, d, J=8.30 Hz), 7.23–7.35 (5H, m), 7.40 (1H, d, J=1.96 Hz), 7.46 (1H, dd, J=8.30, 1.96 Hz), 9.83 (1H, s)

(2) 4-methoxy-3-phenetyloxybenzylidene malonic acid diethyl ester

Using the same procedure as in Example 1(1), 4-methoxy-3-phenethyloxybenzaldehyde, instead of 3,4- dimethoxybenzaldehyde, was used to obtain 4-methoxy-3-phenethyloxybenzylidenemalonic acid diethyl ester.

$^1$H-NMR (CDCl$_3$, 400 MHz) δ1.25 (3H, t, J=7.32 Hz), 1.32 (3H, t, J=7.32 Hz), 3.16 (2H, t, J=7.82 Hz), 3.90 (3H, s), 4.18 (2H, t, J=7.82 Hz), 4.27 (2H, q, J=7.32 Hz), 4.28 (2H, q, J=7.32 Hz), 6.86 (1H, d, J=8.30 Hz), 7.03 (1H, d, J=1.95 Hz), 7.09 (1H, dd, J=8.30, 1.95 Hz), 7.23–7.35 (5H, m), 7.62 (1H, s)

(3) 4,4-diethoxy-2-ethoxycarbonyl-3-(4-methoxy-3-phenethyloxyphenyl)butyric acid ethyl ester Using the same procedure as in Example 1(2), 4-methoxy-3-phenethyloxybenzylidenemalonic acid diethyl ester, instead of 3,4-dimethoxybenzylidenemalonic acid diethyl ester, was used to obtain 4,4-diethoxy-2-ethoxycarbonyl-3-(4-methoxy-3-phenethyloxyphenyl)butyric acid ethyl ester (yield 64.6%).

(4) 5-(4-methoxy-3-phenethyloxyphenyl)-2,3,4,5-tetrahydropyridazin-3-one

Using the same procedure as in Example 1 (3), 4,4-diethoxy-2-ethoxycarbonyl-3-(4-methoxy-3-phenethyloxyphenyl)butyric acid ethyl ester, instead of 3-(3,4-dimethoxyphenyl)-4,4-diethoxy-2-ethoxycarbonyl butyric acid ethyl ester, was used to obtain a light yellow solid of above-described compound (51.4%) via 4,4-diethoxy-3-(4-methoxy-3-phenethyloxyphenyl)butyric acid (yield 51.4%).

$^1$H-NMR (CDCl$_3$, 400 MHz) δ2.58(1H, dd, J=17.09, 11.72 Hz), 2.78 (1H, dd, J=17.09, 7.81 Hz), 3.17 (2H, t, J=7.33 Hz), 3.75 (1H, ddd, J=11.72, 7.81, 2.45 Hz), 3.87 (3H, s), 4.21 (2H, t, J=7.33 Hz), 6.67 (1H, d, J=1.95 Hz), 6.76 (1H, dd, J=8.30, 1.95 Hz), 6.87 (1H, d, J=8.30 Hz), 7.13 (1H, d, J=2.45 Hz), 7.28–7.35 (5H, m), 8.41 (1H, broad s)

Example 9

Synthesis of 5-[3-(2-indanyloxy)-4-methoxyphenyl]-2,3,4,5-tetrahydropyridazin-3-one (Compound No. 9 shown in Table 1)

(1) 3-(2-indanyloxy)-4-methoxybenzaldehyde

Using the same procedure as in Example 8(1), 2-indanol, instead of phenethyl alcohol, was used to obtain 3-(2-indanyloxy)-4-methoxybenzaldehyde (yield 62.6%) as a light yellow solid.

$^1$H-NMR (CDCl$_3$, 400 MHz) δ3.25 (2H, dd, J=16.60, 3.42 Hz), 3.46 (2H, dd, J=16.60, 6.35 Hz), 3.90 (3H, s), 5.26 (1H, m), 6.98 (1H, d, J=8.30 Hz), 7.17–7.21 (2H, m), 7.22–7.25 (2H, m), 7.46–7.49 (2H, m), 9.87 (1H, s)

(2) 3-(2-indanyloxy)-4-methoxybenzylidenemalonic acid diethyl ester

Using the same procedure as in Example 1 (1), 3-(2-indanyloxy)-4-methoxybenzaldehyde, instead of 3,4-dimethoxybenzaldehyde, was used to obtain 3-(2-indanyloxy)-4-methoxybenzylidenemalonic acid diethyl ester.

$^1$H-NMR (CDCl$_3$, 400 MHz) δ1.32 (3H, t, J=7.33 Hz), 1.33 (3H, t, J=7.33 Hz), 3.22 (2H, dd, J=16.60, 3.90 Hz), 3.40 (2H, dd, J=16.60, 6.84 Hz), 3.85 (3H, s), 4.30 (2H, q, J=7.33 Hz), 4.35 (2H, q, J=7.33 Hz), 5.14 (1H, m), 6.86 (1H, d, J=8.79 Hz), 7.10–7.11 (2H, m), 7.17–7.25 (4H, m), 7.66 (1H, s)

(3) 4,4-diethoxy-2-ethoxycarbonyl-3-[3-(2-indanyloxy)-4-methoxyphenyl]butyric acid ethyl ester Using the same procedure as in Example 1(2), 3-(2-indanyloxy)-4-methoxybenzylidenemalonic acid diethyl ester, instead of 3,4-dimethoxybenzylidenemalonic acid diethyl ester, was used to obtain 4,4-diethoxy-2-ethoxycarbonyl-3-[3-(2-indanyloxy)-4-methoxyphenyl]butyric acid ethyl ester (yield 74.6%).

(4) 5-[3-(2-indanyloxy)-4-methoxyphenyl]-2,3,4,5-tetrahydropyridazin-3-one

Using the same procedure as in Example 1(3), 4,4-diethoxy-2-ethoxycarbonyl-3-[3-(2-indanyloxy)-4-methoxyphenyl]butyric acid ethyl ester, instead of 3-(3,4-dimethoxyphenyl)-4,4-diethoxy-2-ethoxycarbonylbutyric acid ethyl ester, was used to obtain a white solid of the above-described compound (yield 53.6%) via 4,4-diethoxy-3-[3-(2-indanyloxy)-4-methoxyphenyl]butyric acid.

$^1$H-NMR (CDCl$_3$, 400 MHz) δ2.63 (1H, dd, J=17.09, 11.23 Hz), 2.83 (1H, dd, J=17.09, 7.81 Hz), 3.23 (2H, dd, J=16.60, 3.90 Hz), 3.36 (2H, dd, J=16.60, 6.35 Hz), 3.80 (1H, m), 3.82 (3H, s), 5.18 (1H, m), 6.77 (1H, d, J=1.95 Hz), 6.80 (1H, dd, J=8.30, 1.95 Hz), 6.88 (1H, d, J=8.30 Hz), 7.17–7.26 (5H, m), 8.41 (1H, broad s)

Example 10

Synthesis of 5-(3-cyclopropylmethyloxy-4-methoxyphenyl)-2,3,4,5-tetrahydropyridazin-3-one (Compound No. 10 shown in Table 1)

(1) 3-cyclopropylmethyloxy-4-methoxybenzaldehyde

Using the same procedure as in Example 8 (1), cyclopropylcarbinol, instead of phenethyl alcohol, was used to obtain a white solid of 3-cyclopropylmethyloxy-4-methoxybenzaldehyde (yield 77.4%).

$^1$H-NMR (CDCl$_3$, 400 MHz) δ0.36–0.40 (2H, m), 0.65–0.70 (2H, m), 1.34–1.38 (1H, m), 3.92 (2H, d, J=6.84 Hz), 3.97 (3H, s), 6.98 (1H, d, J=8.30 Hz), 7.39 (1H, d, J=1.95 Hz), 7.45 (1H, dd, J=8.30, 1.95 Hz), 9.84 (1H, s)

(2) 3-cyclopropylmethyloxy-4-methoxybenzylidene malonic acid diethyl ester

Using the same procedure as in Example 1 (1), 3-cyclopropylmethyloxy-4-methoxybenzaldehyde, instead of 3,4-dimethoxybenzaldehyde, was used to obtain 3-cyclopropylmethyloxy-4-methoxybenzylidenemalonic acid diethyl ester.

$^1$H-NMR (CDCl$_3$, 400 MHz) δ0.34–0.38 (2H, m), 0.63–0.68 (2H, m), 1.32 (6H, t, J=7.33 Hz), 1.30–1.35 (1H, m), 3.83 (2H, d, J=7.32 Hz), 3.90 (3H, s), 4.29 (2H, q, J=7.32 Hz), 4.34 (2H, q, J=7.32 Hz), 6.86 (1H, d, J=8.30 Hz), 7.02 (1H, d, J=1.95 Hz), 7.08 (1H, dd, J=8.30, 1.95 Hz), 7.63 (1H, s)

(3) 3-(3-cyclopropylmethyloxy-4-methoxyphenyl)-4,4-diethoxy-2-ethoxycarbonylbutyric acid ethyl ester Using the same procedure as in Example 1 (2), 3-cyclopropylmethyloxy-4-methoxybenzylidenemalonic acid diethyl ester, instead of 3,4-dimethoxybenzylidenemalonic acid diethyl ester, was used to obtain 3-(cyclopropylmethyloxy-4-methoxyphenyl)-4,4-diethoxy-2-ethoxycarbonylbutyric acid ethyl ester (yield 90.6%).

(4) 5-(3-cyclopropylmethyloxy-4-methoxyphenyl)-2,3,4,5-tetrahydropyridazin-3-one Using the same procedure as in Example 1(3), 3-(3-cyclopropylmethyloxy-4-methoxyphenyl)-4,4-diethoxy-2- ethoxycarbonylbutyric acid ethyl ester, instead of 3-(3,4-dimethoxyphenyl)-4,4-diethoxy-2-ethoxycarbonylbutyric acid ethyl ester, was used to obtain a yellow solid of the above-described compound (yield 43.0%) via 3-(3-cyclopropylmethyloxy-4-methoxyphenyl)-4,4-diethoxybutyric acid.

$^1$H-NMR (CDCl$_3$, 400 MHz) δ0.34–0.38 (2H, m), 0.63–0.68 (2H, m), 1.28–1.35 (1H, m), 2.61 (1H, dd, J=17.09, 11.72 Hz), 2.80 (1H, dd, J=17.09, 7.81 Hz), 3.77 (1H, ddd, J=11.72, 7.81, 2.44 Hz), 3.85 (2H, d, J=7.32 Hz), 3.87 (3H, s), 6.71 (1H, d, J=2.44 Hz), 6.77 (1H, dd, J=8.30, 2.44 Hz), 6.87 (1H, d, J=8.30 Hz), 7.16 (1H, d, J=2.44 Hz), 8.46 (1H, broad s)

Example 11

Synthesis of 5-[4-methoxy-3-[(1-methylcyclopropyl)methyloxy]phenyl]2,3,4,5-tetrahydropyridazin-3-one (Compound No. 11 shown in Table (1)

(1) 4-methoxy-3-[(1-methylcyclopropyl) methyloxy]benzaldehyde

Using the same procedure as in Example 8(1), (1-methylcyclopropyl)carbinol, instead of phenethyl alcohol, was used to obtain yellow oily 4-methoxy-3-[(1-methylcyclopropyl) methyloxy]benzaldehyde (yield 65.0%).

$^1$H-NMR (CDCl$_3$, 400 MHz) δ0.45–0.47 (2H, m), 0.56–0.57 (2H, m), 1.27 (3H, s), 3.84 (2H, s), 3.95 (3H, s), 6.97 (1H, d, J=8.30 Hz), 7.37 (1H, broad), 7.45 (1H, dd, J=8.30, 1.46 Hz), 9.83 (1H, s)

(2) 4-methoxy-3-[(1-methylcyclopropyl) methyloxy]benzylidenemalonic acid diethyl ester Using the same procedure as in Example 1(1), 4-methoxy-3-[(1-methylcyclopropyl)methyloxy]benzaldehyde, instead of 3,4-dimethoxybenzaldehyde, was used to obtain 4-methoxy-3-[(1-methylcyclopropyl) methyloxy] benzylidenemalonic acid diethyl ester.

$^1$H-NMR (CDCl$_3$, 400 MHz) δ0.44 (2H, m), 0.54 (2H, m), 1.26 (3H, s), 1.32 (6H, t, J=7.32 Hz), 3.74 (2H, s), 3.89 (3H, s), 4.29 (2H, q, J=7.32 Hz), 4.34 (2H, q, J=7.32 Hz), 6.85 (1H, d, J=8.30 Hz), 6.99 (1H, d, J=1.95 Hz), 7.08 (1H, dd, J=8.30, 1.95 Hz), 7.63 (1H, s)

(3) 4,4-diethoxy-2-ethoxycarbonyl-3-[4-methoxy-3-[(1-methylcyclopropyl)methyloxy]phenyl]butyric acid ethyl ester Using the same procedure as in Example 1 (2), 4-methoxy-3-[(1-methylcyclopropyl)methyloxy]benzylidene malonic acid diethyl ester, instead of 3,4-dimethoxybenzylidenemalonic acid diethyl ester, was used to obtain 4,4-diethoxy-2-ethoxycarbonyl-3-[4-methoxy-3-[(1-methylcyclopropyl)methyloxy]phenyl]butyric acid ethyl ester (yield 53.8%).

(4) 5-[4-methoxy-3-[(1-methylcyclopropyl) methyloxy]phenyl]-2,3,4,5-tetrahydropyridazin-3-one Using the same procedure as in Example 1 (3), 4,4-diethoxy-2-ethoxycarbonyl-3-[4-methoxy-3-[(1-methylcyclopropyl)methyloxy]phenyl]butyric acid ethyl ester, instead of 3-(3,4-dimethoxyphenyl)-4,4-diethoxy-2-ethoxycarbonylbutyric acid ethyl ester, was used to obtain a white solid of the above-described compound (yield 48.8%) via 4,4-diethoxy-3-[4-methoxy-3-[(1-methylcyclopropyl)methyloxy]phenyl]butyric acid.

$^1$H-NMR (CDCl$_3$, 400 MHz) δ0.43–0.45 (2H, m), 0.53–0.56 (2H, m), 1.26 (3H, s), 2.61 (1H, dd, J=17.09, 11.23 Hz), 2.80 (1H, dd, J=17.09, 7.32 Hz), 3.74–3.80 (1H, m), 3.77 (2H, s), 3.86 (3H, s), 6.70 (1H, d, J=1.95 Hz), 6.76 (1H, dd, J=8.30, 1.95 Hz), 6.87 (1H, d, J=8.30 Hz), 7.16 (1H, d, J=1.96 Hz), 8.52 (1H, broad s)

Example 12

Synthesis of 5-[4-methoxy-3-(2-methylpropoxy)phenyl]-2,3,4,5-tetrahydropyridazin-3-one (Compound No. 12 shown in Table 1)

(1) 4-methoxy-3-(2-methylpropoxy)benzaldehyde

Using the same procedure as in Example 8(1), isobutyl alcohol, instead of phenethyl alcohol, was used to obtain a yellow oily 4-methoxy-3-(2-methylpropoxy)benzaldehyde (yield 75.8%).

$^1$H-NMR (CDCl$_3$, 400 MHz) δ1.05 (6H, d, J=6.83 Hz), 2.19 (1H, m, J=6.83 Hz), 3.83 (2H, d, J=6.83 Hz), 3.95 (3H, s ), 6.97 (1H, d, J=7.81 Hz), 7.40 (1H, d, J=1.46 Hz), 7.44 (1H, dd, J=7.81, 1.46 Hz), 9.84 (1H, s)

(2) 4-methoxy-3-(2-methylpropoxy)benzylidenemalonic diethyl ester

Using the same procedure as in Example 1 (1), 4-methoxy-3-(2-methylpropoxy)benzaldehyde, instead of 3,4-dimethoxybenzaldehyde, was used to obtain 4-methoxy-3-(2-methylpropoxy)benzylidenemalonic acid diethyl ester.

$^1$H-NMR (CDCl$_3$, 400 MHz) δ1.03 (6H, d, J=6.34 Hz), 1.33 (3H, t, J=6.83 Hz), 1.33 (3H, t, J=6.83 Hz), 2.16 (1H, m), 3.74 (2H, d, J=6.84 Hz), 3.89 (3H, s), 4.29 (2H, q, J=6.83 Hz), 4.35 (2H, q, J=6.83 Hz), 6.85 (1H, d, J=8.30 Hz), 7.02 (1H, d, J=1.95 Hz), 7.07 (1H, dd, J=8.30, 1.95 Hz), 7.64 (1H, s)

(3) 4,4-diethoxy-2-ethoxycarbonyl-3-[4-methoxy-3-(2-methylpropoxy)phenyl]butyric ethyl ester Using the same procedure as in Example 1 (2), 4-methoxy-3-(2-methylpropoxy)benzylidenemalonic acid diethyl ester, instead of 3,4-dimethoxybenzylidene malonic acid diethyl ester, was used to obtain 4,4-diethoxy-2-ethoxycarbonyl-3-[4-methoxy-3-(2-methylpropoxy)phenyl]butyric acid ethyl ester (yield 55.1%).

(4) 5-[4-methoxy-3-(2-methylpropoxy)phenyl]-2,3,4,5-tetrahydropyridazin-3-one

Using the same procedure as in Example 1 (3), 4,4-diethoxy-2-ethoxycarbonyl-3-[4-methoxy-3-(2-methylpropoxy)phenyl]butyric acid ethyl ester, instead of 3-(3,4-dimethoxyphenyl)-4,4-diethoxy-2-ethoxycarbonylbutyric acid ethyl ester, was used to obtain a light yellow solid of the above-described compound via 4,4-diethoxy-3-[4-methoxy-3-(2-methylpropoxy)phenyl]butyric acid (yield 48.6%).

$^1$H-NMR (CDCl$_3$, 400 MHz) δ1.04 (6H, d, J=6.83 Hz), 2.16 (1H, m, J=6.83 Hz), 2.62 (1H, dd, J=17.09, 11.72 Hz), 2.81 (1H, dd, J=17.09, 7.81 Hz), 3.76 (2H, d, J=6.83 Hz), 3.78 (1H, ddd, J=11.72, 7.81, 1.95 Hz), 3.86 (3H, s), 6.71 (1H, d, J=2.44 Hz), 6.75 (1H, dd, J=8.30, 2.44 Hz), 6.87 (1H, d, J=8.30 Hz), 7.17 (1H, d, J=1.95 Hz), 8.44 (1H, broad s)

Example 13

Synthesis of 5-(3-butoxy-4-methoxyphenyl)-2,3,4,5-tetrahydropyridazin-3-one (Compound No. 13 shown in Table (1)

(1) 3-butoxy-4-methoxybenzaldehyde

Using the same procedure as in Example 8(1), butanol, instead of phenethyl alcohol, was used to obtain 3-butoxy-4-methoxybenzaldehyde (yield 99.0%).

¹H-NMR (CDCl₃, 400 MHz) δ0.99 (3H, t, J=7.32 Hz), 1.46–1.55 (2H, m), 1.82–1.89 (2H, m), 3.95 (3H, s), 4.08 (2H, t, J=6.83 Hz), 6.98 (1H, d, J=7.81 Hz), 7.40–7.46 (2H, m)

(2) 3-butoxy-4-methoxybenzylidenemalonic acid diethyl ester

Using the same procedure as in Example 1(1), 3-butoxy-4-methoxybenzaldehyde, instead of 3,4-dimethoxybenzaldehyde, was used to obtain 3-butoxy-4-methoxybenzylidenemalonic acid diethyl ester.

¹H-NMR (CDCl₃, 400 MHz) δ0.98 (3H, t, J=7.32 Hz), 1.33 (6H, t, J=7.32 Hz), 1.49 (2H, q, J=7.32 Hz), 1.83 (2H, m, J=7.32 Hz), 3.89 (3H, s), 3.99 (2H, t, J=7.32 Hz), 4.29 (2H, q, J=7.33 Hz), 4.35 (2H, q, J=7.33 Hz), 6.85 (1H, d, J=8.30 Hz), 7.03 (1H, d, J=1.95 Hz), 7.07 (1H, dd, J=8.30, 1.95 Hz), 7.64 (1H, s)

(3) 3-(3-butoxy-4-methoxyphenyl)-4,4-diethoxy-2-ethoxycarbonylbutyric acid ethyl ester Using the same procedure as in Example 1(2), 3-butoxy-4-methoxybenzylidenemalonic acid diethyl ester, instead of 3,4-dimethoxybenzylidenemalonic acid diethyl ester, was used to obtain 3-(3-butoxy-4-methoxyphenyl)-4,4-diethoxy-2-ethoxycarbonylbutyric acid ethyl ester (yield 64.2%).

(4) 5-(3-butoxy-4-methoxyphenyl)-2,3,4,5-tetrahydropyridazin-3-one

Using the same procedure as in Example 1(3), 3-(3-butoxy-4-methoxyphenyl)-4,4-diethoxy-2-ethoxycarbonylbutyric acid ethyl ester, instead of 3-(3,4-dimethoxyphenyl)-4,4-diethoxy-2-ethoxycarbonylbutyric acid ethyl ester, was used to obtain a yellow solid of the above-described compound via 3-(3-butoxy-4-methoxyphenyl)-4,4-diethoxybutyric acid (yield 47.5%).

¹H-NMR (CDCl₃, 400 MHz) δ0.98 (3H, t, J=7.33 Hz), 1.50 (2H, m), 1.83 (2H, m), 2.62 (1H, dd, J=17.09, 11.72 Hz), 2.81 (1H, dd, J=17.09, 7.82 Hz), 3.79 (1H, ddd, J=11.72, 7.82, 1.95 Hz), 3.86 (3H, s), 4.01 (2H, t, J=6.84 Hz), 6.72 (1H, d, J=1.95 Hz), 6.76 (1H, dd, J=8.30, 1.95 Hz), 6.86 (1H, d, J=8.30 Hz), 7.18 (1H, d, J=1.95 Hz), 8.63 (1H, broad s)

Example 14

Synthesis of 5-[3-(2-ethylbutoxy)-4-methoxyphenyl]-2,3,4,5-tetrahydropyridazin-3-one (Compound No. 14 shown in Table 1)

(1) 3-(2-ethylbutoxy)-4-methoxybenzaldehyde

Using the same procedure as in Example 8(1), 2-ethylbutanol, instead of phenethyl alcohol, was used to obtain colorless oily 3-(2-ethylbutoxy)-4-methoxybenzaldehyde (yield 78.4%).

¹H-NMR (CDCl₃, 400 MHz) δ0.94 (6H, t, J=7.32 Hz), 1.43–1.56 (4H, m), 1.80 (1H, m), 3.94 (3H, s), 3.94 (2H, d, J=6.35 Hz), 6.97 (1H, d, J=7.82 Hz), 7.41 (1H, d, J=1.95 Hz), 7.44 (1H, dd, J=7.82, 1.95 Hz), 9.85 (1H, s)

(2) 3-(2-ethylbutoxy)-4-methoxybenzylidenemalonic acid diethyl ester

Using the same procedure as in Example 1(1), 3-(2-ethylbutoxy)-4-methoxybenzaldehyde, instead of 3,4-dimethoxybenzaldehyde, was used to obtain 3-(2-ethylbutoxy)-4-methoxybenzylidenemalonic acid diethyl ester.

¹H-NMR (CDCl₃, 400 MHz) δ0.93 (6H, t, J=7.32 Hz), 1.33 (6H, t, J=7.32 Hz), 1.42–1.55 (4H, m), 1.77 (1H, m), 3.85 (2H, d, J=6.35 Hz), 3.88 (3H, s), 4.29 (2H, q, J=7.32 Hz), 4.35 (2H, q, J=7.32 Hz), 6.85 (1H, d, J=8.30 Hz), 7.03 (1H, d, J=1.95 Hz), 7.07 (1H, dd, J=8.30, 1.95 Hz), 7.65 (1H, s)

(3) 4,4-diethoxy-2-ethoxycarbonyl-3-[3-(2-ethylbutoxy)-4-methoxyphenyl]butyric acid ethyl ester Using the same procedure as in Example 1 (2), 3-(2-ethylbutoxy)-4-methoxybenzylidenemalonic acid diethyl ester, instead of 3,4-dimethoxybenzylidenemalonic acid diethyl ester, was used to obtain 4,4-diethoxy-2-ethoxycarbonyl-3-[3-(2-ethylbutoxy)-4-methoxyphenyl] butyric ethyl ester (yield 68.5%).

(4) 5-[3-(2-ethylbutoxy)-4-methoxyphenyl]-2,3,4,5-tetrahydropyridazin-3-one

Using the same procedure as in Example 1(3), 4,4-diethoxy-2-ethoxycarbonyl-3-[3-(2-ethylbutoxy)-4-methoxyphenyl]butyric acid ethyl ester, instead of 3-(3,4-dimethoxyphenyl)-4,4-diethoxy-2-ethoxycarbonylbutyric acid ethyl ester, was used to obtain a yellow solid of the above-described compound via 4,4-diethoxy-3-[3-(2-ethylbutoxy)-4-methoxyphenyl] butyric acid (yield 36.9%).

¹H-NMR (CDCl₃, 400 MHz) δ0.94 (6H, t, J=7.32 Hz), 1.42–1.54 (4H, m), 1.76 (1H, m, J=6.35 Hz), 2.63 (1H, dd, J=17.09, 11.71 Hz), 2.81 (1H, dd, J=17.09, 7.33 Hz), 3.78 (1H, m), 3.85 (3H, s), 3.87 (2H, d, J=6.35 Hz), 6.72 (1H, d, J=1.95 Hz), 6.75 (1H, dd, J=8.30, 1.95 Hz), 6.87 (1H, d, J=8.30 Hz), 7.18 (1H, broad s), 8.44 (1H, broad s)

Example 15

Synthesis of 5-[3-(2,2-dimethylpropoxy)-4-methoxyphenyl]-2,3,4,5-tetrahydropyridazin-3-one (Compound No. 15 shown in Table 1)

(1) 3-(2,2-dimethylpropoxy)-4-methoxybenzaldehyde

Using the same procedure as in Example 8(1), 2,2-dimethylpropanol, instead of phenethyl alcohol, was used to obtain yellow oily 3-(2,2-dimethylpropoxy)-4-methoxybenzaldehyde (yield 34.8%).

¹H-NMR (CDCl₃, 400 MHz) δ1.07 (9H, s), 3.70 (2H, s), 3.94 (3H, s), 6.96 (1H, d, J=8.30 Hz), 7.39 (1H, d, J=1.95 Hz), 7.43 (1H, dd, J=8.30, 1.95 Hz), 9.84 (1H, s)

(2) 3-(2,2-dimethylpropoxy)-4-methoxybenzylidene malonic acid diethyl ester Using the same procedure as in Example 1(1), 3-(2,2-dimethylpropoxy)-4-methoxybenzaldehyde, instead of 3,4-dimethoxybenzaldehyde, was used to obtain 3-(2,2-dimethylpropoxy)-4-methoxybenzylidenemalonic acid diethyl ester.

¹H-NMR (CDCl₃, 400 MHz) δ1.05 (9H, s), 1.33 (3H, t, J=7.33 Hz), 1.34 (3H, t, J=7.33 Hz), 3.60 (2H, s), 3.88 (3H, s), 4.29 (2H, q, J=7.33 Hz), 4.35 (2H, q, J=7.33 Hz), 6.84 (1H, d, J=8.30 Hz), 7.00 (1H, d, J=1.95 Hz), 7.06 (1H, dd, J=8.30, 1.95 Hz), 7.64 (1H, s)

(3) 3-[3-(2,2-dimethylpropoxy)-4-methoxyphenyl]-4,4-diethoxy-2-ethoxycarbonylbutyric acid ethyl ester Using the same procedure as in Example 1(2), 3-(2,2-dimethylpropoxy)-4-methoxybenzylidenemalonic acid diethyl ester, instead of 3,4-dimethoxybenzylidenemalonic acid diethyl ester, was used to obtain 3-[3-(2,2-dimethylpropoxy)-4-methoxyphenyl]-4,4-diethoxy-2-ethoxycarbonylbutyric acid ethyl ester (yield 62.6%).

(4) 5-[3-(2,2-dimethylpropoxy)-4-methoxyphenyl]-2,3,4,5-tetrahydropyridazin-3-one Using the same procedure as in Example 1(3), 3-[3-(2,2-dimethylpropoxy)-4-methoxyphenyl]-4,4-diethoxy-2-ethoxycarbonylbutyric acid ethyl ester, instead of 3-(3,4-dimethoxyphenyl)-4,4-diethoxy-2-ethoxycarbonylbutyric acid ethyl ester, was used to obtain a light yellow solid of the above-referenced compound via 3-[3-(2,2-dimethylpropoxy)-4-methoxyphenyl]-4,4-diethoxybutyric acid (yield 68.7%).

$^1$H-NMR (CDCl$_3$, 400 MHz) δ1.06 (9H, s), 2.62 (1H, dd, J=17.09, 11.72 Hz), 2.81 (1H, dd, J=17.09, 7.82 Hz), 3.62 (2H, s), 3.78 (1H, ddd, J=11.72, 7.82, 2.44 Hz), 3.85 (3H, s), 6.71 (1H, d, J=1.95 Hz), 6.74 (1H, dd, J=8.30, 1.95 Hz), 6.87 (1H, d, J=8.30 Hz), 7.17 (1H, d, J=2.44 Hz), 8.43 (1H, broad s)

Example 16

Synthesis of 5-[4-methoxy-3-(5-phenylpentyloxy) phenyl]-2,3,4,5-tetrahydropyridazin-3-one (Compound No. 16 shown in Table 1)

(1) 4-methoxy-3-(5-phenylpentyloxy)benzaldehyde

Using the same procedure as in Example 8 (1), 5-phenylpentanol, instead of phenethyl alcohol, was used to obtain light yellow solid of 4-methoxy-3-(5-phenylpentyloxy)benzaldehyde (yield 81.4%).

$^1$H-NMR (CDCl$_3$, 400 MHz) δ1.47–1.59 (2H, m), 1.67–1.75 (2H, m), 1.87–1.94 (2H, m), 2.65 (2H, t, J=7.81 Hz), 3.94 (3H, s), 4.07 (2H, t, J=6.83 Hz), 6.96–7.56 (8H, m), 9.84 (1H, s)

(2) 4-methoxy-3-(5-phenylpentyloxy)benzylidene malonic acid diethyl ester

Using the same procedure as in Example 1(1), 4-methoxy-3-(5-phenylpentyloxy)benzaldehyde, instead of 3,4-dimethoxybenzaldehyde, was used to obtain 4-methoxy-3-(5-phenylpentyloxy)benzylidenemalonic acid diethyl ester.

$^1$H-NMR (CDCl$_3$, 400 MHz) δ1.29–1.34 (6H, m), 1.47–1.55 (2H, m), 1.66–1.74 (2H, m), 1.84–1.92 (2H, m), 2.65 (2H, t, J=7.81 Hz), 3.88 (3H, s), 3.98 (2H, t, J=6.83 Hz), 4.27–4.36 (4H, m), 6.85 (1H, d, J=8.30 Hz), 7.01 (1H, d, J=1.95 Hz), 7.08 (1H, dd, J=8.30, 1.95 Hz), 7.17–7.36 (5H, m), 7.64 (1H, s)

(3) 4,4-diethoxy-2-ethoxycarbonyl-3-[4-methoxy-3-(5-phenylpentyloxy)phenyl]butyric acid ethyl ester Using the same procedure as in Example 1(2), 4-methoxy-3-(5-phenylpentyloxy)benzylidenemalonic acid diethyl ester, instead of 3,4-dimethoxybenzylidene malonic acid diethyl ester, was used to obtain 4,4-diethoxy-2-ethoxycarbonyl-3-[4-methoxy-3-(5-phenylpentyloxy) phenyl]butyric acid ethyl ester (yield 61.4%).

(4) 5-[4-methoxy-3-(5-phenylpentyloxy)phenyl]-2,3,4,5-tetrahydropyridazin-3-one

Using the same procedure as in Example 1(3), 4,4-diethoxy-2-ethoxycarbonyl-3-[4-methoxy-3-(5-phenylpentyloxy)phenyl]butyric acid ethyl ester, instead of 3-(3,4-dimethoxyphenyl)-4,4-diethoxy-2-ethoxycarbonylbutyric acid ethyl ester, was used to obtain a light yellow solid of the above-described compound via 4,4-diethoxy-3-[3-(5-phenylpentyloxy)-4-methoxyphenylbutyric acid (yield 58.6%).

$^1$H-NMR (CDCl$_3$, 400 MHz) δ1.50–1.58 (2H, m), 1.67–1.74 (2H, m), 2.58–2.67(3H, m), 2.81 (1H, dd, J=17.09, 7.81 Hz), 3.75–3.80 (1H, m), 3.85 (3H, s), 3.99 (2H, t, J=6.83 Hz), 6.70 (1H, d, J=1.95 Hz), 6.76 (1H, dd, J=8.30, 1.95 Hz), 6.86 (1H, d, J=8.30 Hz), 7.17–7.30 (6H, m), 8.43 (1H, broad s)

Example 17

Synthesis of 5-[3-(2-indanyloxy)-4-methoxyphenyl]-2-methyl-2,3,4,5-tetrahydropyridazin-3-one (Compound No. 17 shown in Table 1)

Using the same procedure as in Example 5, 4,4-diethoxy-3-[3-(2-indanyloxy)-4-methoxyphenyl]butyric acid obtained in Example 9(4), instead of 3-(3-cyclopentyloxy-4-methoxyphenyl)-4,4-diethoxybutyric acid, was used to obtain a light brown solid of the above-described compound (yield 45.7%).

$^1$H-NMR (CDCl$_3$, 400 MHz) δ2.62 (1H, dd, J=16.60, 11.72 Hz), 2.81 (1H, dd, J=16.60, 7.32 Hz), 3.22 (2H, dd, J=16.60, 3.90 Hz), 3.36 (2H, dd, J=16.60, 6.84 Hz), 3.41 (3H, s), 3.77 (1H, m), 3.81 (3H, s), 5.17 (1H, m), 6.75 (1H, d, J=1.96 Hz), 6.78 (1H, dd, J=8.30, 1.96 Hz), 6.87 (1H, d, J=8.30 Hz), 7.17–7.26 (5H, m)

Example 18

Synthesis of 5-(3-cyclopropylmethyloxy-4-methoxyphenyl) -2-methyl-2,3,4,5-tetrahydropyridazin-3-one (Compound No. 18 shown in Table 1)

Using the same procedure as in Example 5, 3-(3-cyclopropylmethyloxy-4-methoxyphenyl) -4,4-diethoxybutyric acid obtained in Example 10(4), instead of 3-(3-cyclopentyloxy-4-methoxyphenyl) -4,4-diethoxy butyric acid, was used to obtain a light yellow solid of the above-described compound (yield 56.1%).

$^1$H-NMR (CDCl$_3$, 400 MHz) δ0.34–0.38 (2H, m), 0.63–0.68 (2H, m), 1.32 (1H, m), 2.60 (1H, dd, J=16.60, 12.71 Hz), 2.79 (1H, dd, J=16.60, 7.33 Hz), 3.40 (3H, s), 3.75 (1H, m), 3.84 (2H, d, J=7.32 Hz), 3.87 (3H, s), 6.69 (1H, d, J=2.44 Hz), 6.75 (1H, dd, J=8.30, 2.44 Hz), 6.87 (1H, d, J=8.30 Hz), 7.18 (1H, d, J=1.47 Hz)

Example 19

5- (4-methoxy-3-phenethyloxyphenyl) -2-methyl-2,3,4,5-tetrahydropyridazin-3-one (Compound No. 19 shown in Table 1)

Using the same procedure as in Example 5, 4,4-diethoxy-3- (4-methoxy-3-phenetyloxyphenyl)butyric acid obtained in Example 8(4), instead of 3-(3-cyclopentyloxy 4-methoxyphenyl)-4,4-diethoxybutyric acid, was used to obtain a yellow solid of the above-described compound (yield 55.6%).

$^1$H-NMR (CDCl$_3$, 400 MHz) δ2.57 (1H, dd, J=16.60, 12.21 Hz), 2.76 (1H, dd, J=16.60, 7.32 Hz), 3.16 (2H, t, J=7.32 Hz), 3.39 (3H, s), 3.72 (1H, ddd, J=12.21, 7.32, 2.44

Hz), 3.86 (3H, s), 4.20 (2H, t, J=7.32 Hz), 6.66 (1H, d, J=1.96 Hz), 6.74 (1H, dd, J=8.30, 1.96 Hz), 6.87 (1H, d, J=8.30 Hz), 7.15 (1H, d, J=2.44 Hz), 7.23–7.34 (5H, m)

Example 20

Synthesis of 5-[4-methoxy-3-(2-methylpropoxy) phenyl]-2-methyl-2,3,4,5-tetrahydropyridazin-3-one (Compound No. 20 shown in Table 1)

Using the same procedure as in Example 5, 4,4-diethoxy-3-[4-methoxy-3-(2-methylpropoxy)phenyl]butyric acid obtained in Example 12(4), instead of 3-(3-cyclopentyloxy-4-methoxyphenyl)-4,4-diethoxybutyric acid, was used to obtain a white solid of the above-described compound (yield 54.2%).

$^1$H-NMR (CDCl$_3$, 400 MHz) δ1.03 (3H, s), 1.05 (3H, s), 2.12–2.19 (1H, m), 2.61 (1H, dd, J=16.60, 12.20 Hz), 2.79 (1H, dd, J=16.60, 7.32 Hz), 3.40 (3H, s), 3.73–3.79 (3H, m), 3.86 (3H, s), 6.70 (1H, d, J=1.95 Hz), 6.73 (1H, dd, J=8.30, 1.95 Hz), 6.86 (1H, d, J=8.30 Hz), 7.19 (1H, d, J=1.95 Hz)

Example 21

Synthesis of 5-[3-(2,2-dimethylpropoxy)-4-methoxyphenyl]-2-methyl-2,3,4,5-tetrahydropyridazin-3-one (Compound No. 21 shown in Table 21)

Using the same procedure as in Example 5, 3-[3-(2,2-dimethylpropoxy)-4-methoxyphenyl]-4,4-diethoxybutyric acid obtained in Example 15(4), instead of 3-(3-cyclopentyloxy-4-methoxyphenyl)-4,4-diethoxybutyric acid, was used to obtain a white solid of the above-described compound (yield 55.0%).

$^1$H-NMR (CDCl3, 400 MHz) δ1.06 (9H, s), 2.60 (1H, dd, J=16.60, 12.21 Hz), 2.78 (1H, dd, J=16.60, 7.32 Hz), 3.40 (3H, s), 3.61 (2H, s), 3.75 (1H, ddd, J=12.21, 7.32, 2.44 Hz), 3.85 (3H, s), 6.69 (1H, d, J=2.44 Hz), 6.73 (1H, dd, J=8.30, 1.95 Hz), 6.86 (1H, d, J=8.30 Hz), 7.19 (1H, d, J=1.95 Hz)

Example 22

Synthesis of 5-[4-methoxy-3-[(1-methylcyclopropyl)methyloxy]phenyl]-2-methyl-2,3,4,5-tetrahydropyridazin-3-one (Compound No. 22 shown in Table 1)

Using the same procedure as in Example 5, 4,4-diethoxy-3-[4-methoxy-3-[(1-methylcyclopropyl) methyloxy]phenyl] butyric acid obtained in Example 11(4), instead of 3-(3-cyclopentyloxy-4-methoxyphenyl)-4,4-diethoxybutyric acid, was used to obtain a yellow solid of the above-described compound (yield 61.6%).

$^1$H-NMR (CDCl$_3$, 400 MHz) δ0.44 (2H, m), 0.54 (2H, m), 1.26 (3H, s), 2.59 (1H, dd, J=16.60, 12.21 Hz), 2.78 (1H, dd, J=16.60, 7.33 Hz), 3.40 (3H, s), 3.75 (1H, ddd, J=12.21, 7.33, 2.45 Hz), 3.77 (2H, s), 3.86 (3H, s), 6.69 (1H, d, J=1.95 Hz), 6.74 (1H, dd, J=8.30, 1.95 Hz), 6.86 (1H, d, J=8.30 Hz), 7.18 (1H, d, J=2.45 Hz)

Example 23

Synthesis of 5-(3-butoxy-4-methoxyphenyl)-2-methyl-2,3,4,5-tetrahydropyridazin-3-one (Compound No. 23 shown in Table 1)

Using the same procedure as in Example 5, 3-(3-butoxy-4-methoxyphenyl)-4,4-diethoxybutyric acid obtained in Example 13(4), instead of 3-(3-cyclopentyloxy-4-methoxyphenyl)-4,4-diethoxybutyric acid, was used to obtain a yellow solid of the above-described compound (yield 59.8%).

$^1$H-NMR (CDCl$_3$, 400 MHz) δ0.98 (3H, t, J=7.33 Hz), 1.50 (2H, m), 1.83 (2H, m), 2.61 (1H, dd, J=16.60, 11.72 Hz), 2.79 (1H, dd, J=16.60, 7.32 Hz), 3.40 (3H, s), 3.76 (1H, ddd, J=11.72, 7.32, 1.95 Hz), 3.86 (3H, s), 4.00 (2H, t, J=6.83 Hz), 6.70 (1H, d, J=1.95 Hz), 6.73 (1H, dd, J=8.30, 1.95 Hz), 6.86 (1H, d, J=8.30 Hz), 7.19 (1H, d, J=1.95 Hz)

Example 24

Synthesis of 5-[4-methoxy-3-(2-ethylbutoxy) phenyl]-2-methyl-2,3,4,5-tetrahydropyridazin-3-one (Compound No. 24 shown in Table 1)

Using the same procedure as in Example 5, 4,4-diethoxy-3-[3-(2-ethylbutoxy)-4-methoxyphenyl]butyric acid obtained in Example 14 (4), instead of 3-(3-cyclopentyloxy-4-methoxyphenyl)-4,4-diethoxybutyric acid, was used to obtain a white solid of the above-described compound (yield 52.5%).

$^1$H-NMR (CDCl$_3$, 400 MHz) δ0.94 (6H, t, J=7.32 Hz), 1.40–1.55 (4H, m), 1.64–1.79 (1H, m), 2.61 (1H, dd, J=16.60, 12.21 Hz), 2.79 (1H, dd, J=16.60, 7.82 Hz), 3.41 (3H, s), 3.76 (1H, ddd, J=12.21, 7.82, 2.45 Hz), 3.85 (3H, s), 3.87 (2H, d, J=5.86 Hz), 6.71 (1H, d, J=1.95 Hz), 6.73 (1H, dd, J=7.81, 1.95 Hz), 6.87 (1H, d, J=7.81 Hz), 7.20 (1H, d, J=2.45 Hz)

Example 25

Synthesis of 5-[4-methoxy-3-[(1-phenylcyclopropyl)methyloxy]phenyl]-2,3,4,5-tetrahydropyridazin-3-one (Compound No. 25 shown in Table 1)

(1) 4-methoxy-3-[(1-phenylcyclopropyl) methyloxy] benzaldehyde

Using the same procedure as in Example 8(1), 1-phenylcyclopropylmethanol, instead of phenethyl alcohol, was used to obtain a yellow oily 4-methoxy-3-[(1-phenylcyclopropyl)methyloxy]benzaldehyde (yield 74.8%).

$^1$H-NMR (CDCl$_3$, 400 MHz) δ1.00–1.02 (2H, m), 1.04–1.07 (2H, m), 3.90 (3H, s), 4.13 (2H, s), 6.93 (1H, d, J=7.81 Hz), 7.19–7.23 (1H, m), 7.28–7.31 (3H, m), 7.41–7.45 (3H, m), 9.79 (1H, s)

(2) 4-methoxy-3-[(1-phenylcyclopropyl)methyloxy] benzylidene malonic acid diethyl ester Using the same procedure as in Example 1(1), 4-methoxy-3-[(1-phenylcyclopropyl)methyloxy] benzaldehyde, instead of 3,4-dimethoxybenzaldehyde, was used to obtain 4-methoxy-3-[(1-phenylcyclopropyl) methyloxty)]benzylidene malonic acid diethyl ester.

$^1$H-NMR (CDCl$_3$, 400 MHz) δ0.98–1.05 (4H, m), 1.28 (3H, t, J=7.33 Hz), 1.32 (3H, t, J=7.33 Hz), 3.84 (3H, s), 4.05 (2H, s), 4.28 (2H, q, J=7.33 Hz), 4.29 (2H, q, J=7.33 Hz), 6.81 (1H, d, J=8.30 Hz), 6.92 (1H, d, J=1.95 Hz), 7.06 (1H, dd, J=8.30, 1.95 Hz), 7.19–7.23 (1H, m), 7.28–7.31 (2H, m), 7.41–7.44 (2H, m), 7.58 (1H, s)

(3) 4,4-diethoxy-2-ethoxycarbonyl-3-[4-methoxy-3-[(1-phenylcyclopropyl)methyloxy]phenyl]butyric acid ethyl ester Using the same procedure as in Example 1 (2), 4-methoxy-3-[(1-phenylcyclopropyl)methyloxy]

benzylidenemalonic acid diethyl ester, instead of 3,4-dimethoxybenzylidenemalonic acid diethyl ester, was used to obtain 4,4-diethoxy-2-ethoxycarbonyl-3-[4-methoxy-3-[(1-phenylcyclopropyl)methyloxy]phenyl]butyric acid ethyl ester (yield 73.2%).

(4) 5-[4-methoxy-3-[(1-phenylcyclopropyl) methyloxy]phenyl]-2,3,4,5-tetrahydropyridazin-3-one Using the same procedure as in Example 1(3), 4,4-diethoxy-2-ethoxycarbonyl-3-[4-methoxy-3-[(1-phenylcyclopropyl)methyloxy]phenyl]butyric acid ethyl ester, instead of 3-(3,4-dimethoxyphenyl)-4,4-diethoxy-2-ethoxycarbonylbutyric acid ethyl ester, was used to obtain a yellow solid of the above-described compound via 4,4-diethoxy-3-[4-methoxy-3-[(1-phenylcyclopropyl) methyloxy]phenyl]butyric acid (yield 65.1%).

$^1$H-NMR (CDCl$_3$, 400 MHz) δ0.97–1.00 (2H, m), 1.03–1.06 (2H, m), 2.52 (1H, dd, J=17.09, 11.72 Hz), 2.73 (1H, dd, J=17.09, 7.81 Hz), 3.69 (1H, ddd, J=11.72, 7.81, 2.44 Hz), 3.80 (3H, s), 4.09 (2H, s), 6.54 (1H, d, J=1.96 Hz), 6.73 (1H, dd, J=8.30, 1.96 Hz), 6.83 (1H, d, J=8.30 Hz), 7.08 (1H, d, J=2.44 Hz), 7.19–7.23 (1H, m), 7.28–7.31 (2H, m), 7.42–7.45 (2H, m), 8.45 (1H, broad s)

Example 26

5-[4-methoxy-3-[(1-phenylcyclopropyl)methyloxy] phenyl]-2-methyl-2,3,4,5-tetrahydropyridazin-3-one (Compound No. 26 shown in Table 1)

Using the same procedure as in Example 5, 4,4-diethoxy-3-[4-methoxy-3-[(1-phenylcyclopropyl) methyloxy]phenyl] butyric acid obtained in Example 25(4), instead of 3-(3-cyclopentyloxy-4-methoxyphenyl)-4,4-diethoxybutyric acid, was used to obtain a yellow solid of the above-described compound (yield 59.5%).

$^1$H-NMR (CDCl$_3$, 400 MHz) δ0.97–1.00 (2H, m), 1.02–1.05 (2H, m), 2.51 (1H, dd, J=16.60, 12.21 Hz), 2.71 (1H, dd, J=16.60, 7.32 Hz), 3.39 (3H, s), 3.66 (1H, ddd, J=12.21, 7.32, 2.44 Hz), 3.79 (3H, s), 4.09 (2H, s), 6.53 (1H, d, J=1.95 Hz), 6.70 (1H, dd, J=8.30, 1.95 Hz), 6.82 (1H, d, J=8.30 Hz), 7.09 (1H, d, J=2.44 Hz), 7.18–7.22 (1H, m), 7.27–7.31 (2H, m), 7.42–7.44 (2H, m)

Example 27

Synthesis of 5-(3,4-dimethoxyphenyl)-6-methyl-2,3,4 5-tetrahydropyridazin-3-one (Compound No.27 shown in Table 1)

(1) 3-(3,4-dimethoxyphenyl)4-oxovaleric acid isopropyl ester 0.12 g (5.30 mM) sodium was dissolved in 5 ml of 2-propanol and the resultant solution was stirred over night at room temperature. 1.00 g (5.15 mM) of 3,4-dimethoxyphenylacetone dissolved in 1 ml of 2-propanol was dropwise added to the solution. The solution was cooled to 0° C. 0.89 g (5.30 mM) of ethyl bromoacetate dissolved in 1 ml of 2-propanol was dropwise added to the solution, and the mixture was stirred for about 2 hours at that temperature. The solution obtained was poured to water and the resultant product was extracted with methylene chloride. The organic extract was dried over anhydrous magnesium sulfate, then the solvent was evaporated in vacuo to obtain a yellow oily crude product. The crude product was purified by chromatography (SiO$_2$: eluted with a gradient of 20% methyl acetate/hexane to 25% methyl acetate/hexane). The solvent was evaporated in vacuo and was dried to obtain 0.67 g of colorless 3-(3,4-dimethoxyphenyl)4-oxovaleric acid isopropyl ester.

(2) 5-(3,4-dimethoxyphenyl)-6-methyl-2,3,4,5-tetrahydropyridazin-3-one 0.67 g (2.28 mM) of 3-(3,4-dimethoxyphenyl)4-oxovaleric acid isopropyl ester and 0.28 ml (5.69 mM) of hydrazine hydrate were added to a mixed solution of 2 ml of acetic acid and 1.3 ml of water and the solution was heated at reflux for 5 hours. The resultant product was poured to an aqueous sodium hydrogencarbonate solution, was extracted with methylene chloride, and was dried over anhydrous magnesium sulfate. The solvent was evaporated in vacuo to obtain a yellow solid residue. The residue was purified by chromatography (SiO$_2$: eluted with 2% methanol/methylene chloride). The solvent was evaporated in vacuo and the resultant product was dried to obtain 0.47 g of a light yellow solid of the above-described compound (yield 83.9%).

$^1$H-NMR (CDCl$_3$, 400 MHz) δ1.96 (3H, s), 2.65 (1H, dd, J=16.60, 5.86 Hz), 2.84 (1H, dd, J=16.60, 7.81 Hz), 3.67 (1H, dd, J=7.81, 5.86 Hz), 3.87 (3H, s), 3.87 (3H, s), 6.66 (1H, d, J=1.95 Hz), 6.72 (1H, dd, J=8.30, 1.95 Hz), 6.83 (1H, d, J=8.30 Hz), 8.57 (1H, broad s)

Example 28

Synthesis of 5-(3-cyclopentyloxy-4-methoxyphenyl)-6-phenyl-2,3,4,5-tetrahydropyridazin-3-one (Compound No. 28 shown in Table 1)

(1) 3-(3-cyclopentyloxy-4-methoxyphenyl)-2-ethoxycarbonyl-3-[2-(2-phenyl-1,3-dithianyl)] propionic acid ethyl ester A solution of 0.72 g (3.65 mM) of 2-phenyl-1,3-dithiane dissolved in 3 ml of dried tetrahydrofuran was cooled to 0° C. A hexane solution of butyl lithium (3.65 mM) was dropwise added to the solution and the mixture was stirred for around 30 minutes at that temperature. The solution was cooled to −78° C. and a solution of 1.00 g (2.76 mM) of 3-cyclopentyloxy-4-methoxybenzylidenemalonic acid diethyl ester dissolved in 7 ml of dried tetrahydrofuran was added. The solution obtained was gradually heated to room temperature, was poured to an aqueous ammonium chloride, and was extracted with diethyl ether. The organic extract was dried over anhydrous magnesium sulfate, then the solvent was evaporated in vacuo to obtain a crude product. The crude product was purified by chromatography (SiO$_2$: eluted with a gradient of 10% hexane/methylene chloride-methylene chloride-2% methanol/methylene chloride). The solvent was evaporated in vacuo and the resultant product was dried to obtain 0.94 g of yellow oily 3-(3-cyclopentyloxy-4-methoxyphenyl)-2-ethoxycarbonyl-3-[2-(2-phenyl-1,3-dithianyl)]propionic acid ethyl ester (yield 61.2%).

(2) 3-benzoyl-3-(3-cyclopentyloxy-4-methoxyphenyl)-2-ethoxycarbonylpropionic acid ethyl ester 1.07 g (6.01 mM) of N-bromosuccinimide and 1.15 g (6.76 mM) of silver nitrate were dissolved in a mixed solution of 46 ml of acetonitrile and 9 ml of water and cooled to 0° C. 2,6-lutidine was dropwise added thereto, then 3-(3-cyclopentyloxy-4-methoxyphenyl)-2-ethoxycarbonyl- 3-[2-(2-phenyl-1,3-dithianyl)]propionic acid ethyl ester dissolved in a mixed solution of acetonitrile and water was dropped to the solution and the resultant mixture stirred for about 30 minutes at the same temperature. 50 ml of sodium sulfite aqueous solution, 50 ml of sodium hydrogencarbonate aqueous solution, and 50 ml of hexane/methylene chloride (1:1) solution were poured continuously in this order to the solution. The solution obtained was stirred for about 30 minutes at room temperature, then filtered through Cerite. The organic layer of the filtrate was dried over anhydrous magnesium sulfate, then the solvent was evaporated in vacuo to obtain a crude product. The crude product was purified by chromatography (SiO$_2$: eluted with methylene chloride). The solvent was evaporated in vacuo to obtain 0.48 g of yellow oily 3-benzoyl-3-(3-cyclopentyloxy-4-methoxyphenyl)-2-ethoxycarbonyl propionic acid ethyl ester (68.6%).

(3) 5-(3-cyclopentyloxy-4-methoxyphenyl)-6-phenyl-2,3,4,5-tetrahydropyridazin-3-one Using the same procedure as in Example 1(3), 3-benzoyl-3-(3-cyclopentyloxy-4-methoxyphenyl)-2-ethoxycarbonylpropionic acid ethyl ester, instead of 3-(3,4-dimethoxyphenyl)-4-4-diethoxy-2-ethoxycarbonylbutyric acid ethyl ester, was used to obtain a white solid of the above-described compound via 3-benzoyl-3-(3-cyclopentyloxy-4-methoxyphenyl) propionic acid (yield 37.8%).

$^1$H-NMR (CDCl$_3$, 400 MHz) δ1.53–1.61 (2H, m), 1.75–1.88 (6H, m), 2.80 (1H, d, J=16.60 Hz), 2.99 (1H, dd, J=16.60, 7.81 Hz), 3.80 (3H, s), 4.41 (1H, d, J=7.81 Hz), 4.65 (1H, m), 6.70–6.80 (3H, m), 7.33–7.37 (3H, m), 7.68–7.71 (2H, m), 8.57 (1H, broad s)

TABLE 1

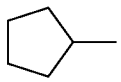

| Compound no. | R$_1$ | R$_2$ | R$_3$ | R$_4$ | R$_5$ | R$_6$ | Dotted line |
|---|---|---|---|---|---|---|---|
| 1 | Me | Me | H | H | H | — | Double bond |
| 2 | Me | Me | Ph | H | H | — | Double bond |
| 3 | 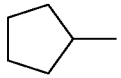 | Me | H | H | H | — | Double bond |
| 4 | 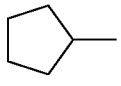 | Me | H | H | H | H | Single bond |
| 5 | 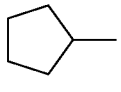 | Me | Me | H | H | — | Double bond |
| 6 | 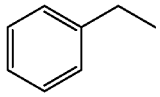 | Me | 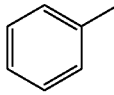 | H | H | — | Double bond |
| 7 | 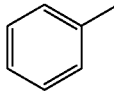 | Me | H | H | H | — | Double bond |
| 8 |  | Me | H | H | H | — | Double bond |

TABLE 1-continued
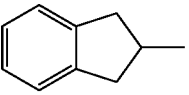
| Compound no. | R₁ | R₂ | R₃ | R₄ | R₅ | R₆ | Dotted line |
|---|---|---|---|---|---|---|---|
| 9 | 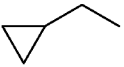 | Me | H | H | H | — | Double bond |
| 10 | 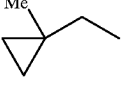 | Me | H | H | H | — | Double bond |
| 11 | 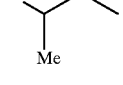 | Me | H | H | H | — | Double bond |
| 12 | 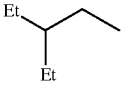 | Me | H | H | H | — | Double bond |
| 13 | n-Bu | Me | H | H | H | — | Double bond |
| 14 | 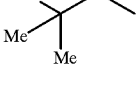 | Me | H | H | H | — | Double bond |
| 15 | 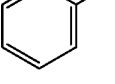 | Me | H | H | H | — | Double bond |
| 16 | 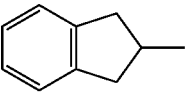 | Me | H | H | H | — | Double bond |
| 17 | 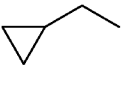 | Me | Me | H | H | — | Double bond |
| 18 | 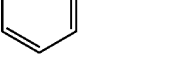 | Me | Me | H | H | — | Double bond |
| 19 | 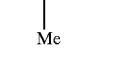 | Me | Me | H | H | — | Double bond |
| 20 |  | Me | Me | H | H | — | Double bond |

TABLE 1-continued

[Structure: R₂O and R₁O substituted phenyl attached to a pyridazinone ring with R₄, R₅, N-R₆, N-R₃ substituents and C=O]

| Compound no. | R₁ | R₂ | R₃ | R₄ | R₅ | R₆ | Dotted line |
|---|---|---|---|---|---|---|---|
| 21 | Me-C(Me)(Me)-CH₂CH₃ (1,1-dimethylpropyl) | Me | Me | H | H | — | Double bond |
| 22 | 1-methylcyclopropyl-ethyl | Me | Me | H | H | — | Double bond |
| 23 | n-Bu | Me | Me | H | H | — | Double bond |
| 24 | CH(Et)(Et) (3-pentyl) | Me | Me | H | H | — | Double bond |
| 25 | 1-phenylcyclopropyl | Me | H | H | H | — | Double bond |
| 26 | 1-phenylcyclopropyl | Me | Me | H | H | — | Double bond |
| 27 | Me | Me | H | H | Me | — | Double bond |
| 28 | cyclopentylmethyl | Me | H | H | Ph | — | Double bond |

Example 29

Preparation of Tablets 30 g of 5-(3-cyclopentyloxy-4-methoxyphenyl)-2,3,4,5-tetrahydropyridazin-3-one (Compound No. 3 in Table 1), 253 g of lactose, 63 g of corn starch, 40 g of low substituted hydroxypropylcellulose, and 4 g of calcium stearate were mixed and compressed using a general method so that the tablets each contained 10 mg of said compound.

Example 30

Preparation of Capsules 30 g of 5-(3-cyclopentyloxy-4-methoxyphenyl)-2,3,4,5-tetrahydropyridazin-3-one (Compound No. 3 in Table 1), 260 g of lactose, 66 g of corn starch, and 4 g of calcium stearate were mixed and filled into gelatin capsules using a general method so that the capsules each contained 10 mg of said compound.

Example 31

Preparation of Inhalations 0.15 g of 5-(3-cyclopentyloxy-4-methoxyphenyl)-2,3,4,5-tetrahydropyridazin-3-one (Compound No. 1 shown in Table 1) pulverized to have a particle size of 1 to 5 μm and 60 g of lactose (325 mesh, D. M. V. Corp.) were mixed. The mixture was filled into capsules so that each capsule contained 50 μg of said compound. A capsule was loaded into a powder inhaler for inhalation.

Text Example 1

Separation of Phosphodiesterase (PDE) and Measurement of PDE Inhibiting Activity Type I, III, IV, and V PDE isozymes were prepared to study the PDE inhibiting activities and selectivities of the compound of the invention [Trends Pharmacol Sci., 12, 19–27 (1992)]. Type I PDE was purchased from Sigma Corp. Type III and V PDE isozymes were partially purified from rats platelets, and type IV PDE isozyme was partially purified from neutrophils. Each enzyme source was homogenized in a buffer (pH 6.5) containing 20 mM bisTris, 2 mM EDTA, 0.1 mM PMSF (phenylmethylsulfonyl fluoride), 5 mM 2-mercaptoethanol, 0.01 mM pepstatin, and 0.01 mM leupeptin and was centrifuged at 30,000G for 30 minutes to obtain a supernatant, which was applied to a column (1.5×20 cm) packed with an ion-exchange resin (Q-sepharose First Flow, Pharmacia Corp.) and was eluted with sodium acetate gradient of 0 to 1M. Partially purified isozymes were identified by observing the effects of conventional inhibitor.

Each PDE isozyme and test compounds dissolved in DMSO (i.e., dimethyl sulfoxide) were added to 50 mM Tris-HCl buffer containing 5 mM magnesium chloride. $^3$H-cAMP (for type III and IV PDE) or $^3$H-cGMP (for type I and V PDE) were added as substrates and were reacted for 30 minutes. The reaction was terminated by placing the test tube in boiling water of 100° C. for 5 minutes. The nucleotides formed by PDE were broken down by 5'-nucleotidase to $^3$H-adenosine or 3H-guanosine. The unreacted substrate and reaction product were separated through a column packed with an ion-exchange resin (QAE sephadex). The eluted $^3$H-nucleoside was measured for its radioactivity by a liquid scintillation counter. The inhibiting activities of the compound of the present invention against types I, III and V are $^1/_{10}$ or less than that against type IV. The inhibiting activities against type IV are shown in Table 2.

TABLE 2

| Compound No. | Type IV PDE Inhibitory activity IC$_{50}$ (M) |
|---|---|
| 1 | $9.3 \times 10^{-6}$ |
| 2 | $4.2 \times 10^{-6}$ |
| 3 | $4.2 \times 10^{-7}$ |
| 4 | $2.5 \times 10^{-6}$ |
| 5 | $6.7 \times 10^{-7}$ |
| 6 | $1.8 \times 10^{-7}$ |
| 7 | $8.7 \times 10^{-6}$ |
| 8 | $1.6 \times 10^{-6}$ |
| 9 | $1.7 \times 10^{-7}$ |
| 10 | $1.6 \times 10^{-6}$ |
| 11 | $1.2 \times 10^{-6}$ |
| 12 | $1.1 \times 10^{-6}$ |
| 13 | $3.4 \times 10^{-6}$ |
| 14 | $2.3 \times 10^{-6}$ |
| 15 | $4.8 \times 10^{-6}$ |
| 16 | $3.3 \times 10^{-7}$ |
| 17 | $6.3 \times 10^{-7}$ |
| 18 | $4.6 \times 10^{-6}$ |
| 19 | $2.7 \times 10^{-6}$ |
| 20 | $2.3 \times 10^{-6}$ |
| 21 | $3.9 \times 10^{-6}$ |
| 22 | $2.7 \times 10^{-6}$ |
| 23 | $6.3 \times 10^{-6}$ |
| 24 | $3.4 \times 10^{-7}$ |
| 25 | $7.5 \times 10^{-7}$ |
| 26 | $1.4 \times 10^{-6}$ |
| 27 | $1.8 \times 10^{-5}$ |
| 28 | $1.9 \times 10^{-5}$ |

Test Example 2

Inhibitory Effects on Activity of Rat Neutrophils

The release of super oxide anions was measured so as to study the inhibitory effects of the compound on inflammatory leukocytes, that is, neutrophils.

Blood sample was obtained from Wister rats anesthetized with ether. It was superposed on a blood cell separation solution (Polymorphoprep 1.113, made by Naicomet Co. (phonetic)) and the neutrophils were separated by centrifugation. The neutrophils were resuspended in a Hank's balanced salt solution at a concentration of $0.5 \times 10^4$ cell/ml. 0.1 mM of Lusigenin and the test substance dissolved in DMSO were added to 2 ml of the cell-suspension. The chemiluminescence generated by stimulation of 0.3 μM calcium ionophore A23187 was measured by a chemiluminescence reader so as to evaluate the release of super oxide anions. The efficacy of the compounds of the present invention was expressed by an IC$_{50}$ value and is shown in Table 3.

TABLE 3

| Compound No. | Action for suppressing release of super oxide anions from rat neutrophils IC$_{50}$ (M) |
|---|---|
| 1 | $1.4 \times 10^{-5}$ |
| 2 | $1.7 \times 10^{-6}$ |
| 3 | $3.0 \times 10^{-8}$ |
| 5 | $4.3 \times 10^{-7}$ |
| 6 | $1.3 \times 10^{-7}$ |
| 27 | $1.5 \times 10^{-5}$ |

Test Example 3

Inhibitory Effect on Antigen-induced Bronchospasm (anti-asthmatic action)

A Hartley male guinea pig was sensitized by intramuscular administration of 35 mg Ovalbumin (OA) on first day and fourth day, and used after 24th day. A trachial canula was introduced in the guinea pig anesthetized with pentobarbital and artificial ventilation was performed 25 to 29 days after the first sensitization. The overflow of the ventilation was measured by the Konzett-Roessler method, while 0.2 mg/kg OA were administered intravenously. The test compound was dissolved in polyethylene glycol 400 and intravenously administered 10 minutes before administration of the antigens. The effect of the present invention was expressed by the ED$_{50}$ value and is shown in Table 4.

TABLE 4

| Compound No. | Action for suppressing antigen-induced bronchospasms ED$_{50}$ (mg/kg) |
|---|---|
| 3 | 0.4 |
| 4 | 2.1 |
| 6 | 3.2 |
| 8 | 4.2 |
| 10 | 0.074 |
| 11 | 0.82 |
| 12 | 1.05 |
| 13 | 1.40 |
| 18 | 0.12 |
| 20 | 0.97 |
| 22 | 2.37 |
| 23 | 0.53 |

Test Example 4

Acute Toxicity Test

Compounds No. 1 to 28 were suspended in an isotonic sodium chloride solution containing 0.5% sodium carboxylmethylcellulose and were administered intraperitoneally in mice. The survival rate the next day was examined. There was no death at a dosage of 30 mg/kg observed in any compound.

Industrial Applicability

As described above, the compound of the present invention exhibits an excellent type IV PDE inhibiting action and is very useful for treating inflammatory diseases such as asthma and dermatitis and autoimmune diseases such as multiple sclerosis and rheumatism.

What is claimed is:

1. A 5-phenyl-3-pyridazinone derivative having the formula (I):

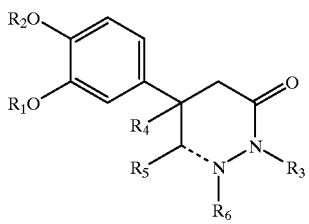

wherein:
R$_1$ represents a C$_1$ to C$_8$ linear or branched alkyl group optionally substituted with a phenyl group or a C$_3$ to C$_6$ cycloalkyl group, which may be further substituted with a C$_1$ to C$_3$ alkyl group; a C$_3$ to C$_7$ cycloalkyl group; or an indanyl group;

R$_2$ represents a C$_1$ to C$_4$ alkyl group;

R$_3$ represents a hydrogen atom; a C$_1$ to C$_5$ linear or branched alkyl group optionally substituted with a substituent selected from the group consisting of phenyl, pyridyl, thiazolyl, furyl, thienyl, naphthyl, and quinolyl; a C$_3$ to C$_7$ cycloalkyl group; or a C$_6$ to C$_{10}$ monocyclic or bicyclic aromatic group or a 5 to 10-membered monocyclic or bicyclic heteroaromatic group selected from the group consisting of phenyl, pyridyl, thiazolyl, furyl, thienyl, naphthyl, and quinolyl; a C$_3$ to C$_7$ cycloalkyl group; or a C$_6$ to C$_{10}$ monocyclic or bicyclic aromatic group or a 5 to 10-membered monocyclic or bicyclic heteroaromatic group selected from the group consisting of phenyl, pyridyl, thiazolyl, furyl, thienyl, naphthyl, and quinolyl;

R$_4$ and R$_5$ each independently represent a hydrogen atom; a C$_1$ to C$_6$ alkyl group; a phenyl group optionally substituted with a methyl or chloro group; or a 5 or 6-membered monocyclic heteroaromatic group selected from the group consisting of pyridyl, thiazolyl, furyl, thienyl and quinolyl;

a dotted line represents a single or double bond, provided that when the dotted line represents a single bond, R$_6$ represents a hydrogen atom or C$_1$ to C$_6$ alkyl group;

an optical isomer thereof, a pharmaceutically acceptable salt thereof, or a hydrate or solvate thereof.

2. A compound as claimed in claim 1, wherein R$_1$ represents a C$_1$ to C$_6$ alkyl group, a C$_1$ to C$_5$ alkyl group substituted with a phenyl, a C$_1$ to C$_5$ alkyl group substituted with a C$_3$ to C$_7$ cycloalkyl group which may be substituted with a C$_1$ to C$_3$ alkyl group; a C$_4$ to C$_6$ cycloalkyl group or indanyl group; R$_2$ represents a methyl or ethyl; R$_3$ represents a hydrogen atom, a C$_1$ to C$_3$ alkyl group, a phenyl, pyridyl, thiazolyl, furyl, thienyl, naphthyl, or quinolyl group, or a C$_1$ to C$_2$ alkyl group substituted with a phenyl, pyridyl, thiazolyl, furyl, thienyl, naphthyl, or quinolyl group; and R$_4$ and R$_5$ independently represent a hydrogen atom, methyl, ethyl, phenyl, or pyridyl.

3. A compound as claimed in claim 1 or 2, wherein R$_1$ represents a methyl, butyl, isobutyl, a C$_1$ to C$_5$ alkyl group substituted with a phenyl, cyclopentyl group, cyclopropylmethyl, (1-methylcyclopropyl)methyl, or 2-indanyl; R$_3$ represents a hydrogen atom, methyl, ethyl, phenyl, or benzyl; and R$_4$ represents a hydrogen atom, methyl, ethyl, phenyl, or pyridyl.

4. A compound as claimed in claim 1, wherein R$_2$ represents a methyl; and R$_5$ represents a hydrogen atom.

5. A compound as claimed in claim 1, wherein the dotted line represents a double bond.

6. A method for treating dermatitis comprising administering a pharmaceutical composition comprising an effective amount of a compound according to claim 1 and a pharmacologically acceptable carrier.

7. A method for preventing or treating asthma comprising administering a pharmaceutical composition comprising an effective amount of a compound according to claim 1 and a pharmacologically acceptable carrier.

* * * * *